(12) United States Patent
Williams

(10) Patent No.: US 12,280,026 B2
(45) Date of Patent: Apr. 22, 2025

(54) USE OF REPIRINAST IN THE PROPHYLAXIS OR TREATMENT OF RENAL FIBROSIS OR KIDNEY DISEASE

(71) Applicant: ALGERNON PHARMACEUTICALS INC., Vancouver (CA)

(72) Inventor: Mark Williams, Winnipeg (CA)

(73) Assignee: ALGERNON PHARMACEUTICALS INC., Vancouver (CA)

( * ) Notice: Subject to any disclaimer, the term of this patent is extended or adjusted under 35 U.S.C. 154(b) by 808 days.

(21) Appl. No.: 17/255,364

(22) PCT Filed: Jun. 25, 2019

(86) PCT No.: PCT/CA2019/050881
§ 371 (c)(1),
(2) Date: Dec. 22, 2020

(87) PCT Pub. No.: WO2020/000092
PCT Pub. Date: Jan. 2, 2020

(65) Prior Publication Data
US 2021/0260000 A1    Aug. 26, 2021

Related U.S. Application Data

(60) Provisional application No. 62/809,330, filed on Feb. 22, 2019, provisional application No. 62/690,738, filed on Jun. 27, 2018.

(51) Int. Cl.
| | | |
|---|---|---|
| A61K 31/4741 | (2006.01) | |
| A61K 31/136 | (2006.01) | |
| A61K 31/167 | (2006.01) | |
| A61K 31/4184 | (2006.01) | |
| A61K 38/18 | (2006.01) | |
| A61K 45/06 | (2006.01) | |
| A61P 13/12 | (2006.01) | |

(52) U.S. Cl.
CPC .......... *A61K 31/167* (2013.01); *A61K 31/136* (2013.01); *A61K 31/4184* (2013.01); *A61K 38/1816* (2013.01); *A61K 45/06* (2013.01); *A61P 13/12* (2018.01)

(58) Field of Classification Search
CPC ...... A61K 31/4741; A61K 45/06; A61P 13/12
See application file for complete search history.

(56) References Cited

FOREIGN PATENT DOCUMENTS

| | | |
|---|---|---|
| JP | 2005-089345 A | 4/2005 |
| JP | 2008-528627 A | 7/2008 |
| JP | 2021-522114 A | 8/2021 |

OTHER PUBLICATIONS

Kobayashi et al., Japan J. Pharmacology, 1993, vol. 63, pp. 73-81. (Year: 1993).*

(Continued)

*Primary Examiner* — Craig D Ricci
*Assistant Examiner* — Janet L Coppins
(74) *Attorney, Agent, or Firm* — Nelson Mullins Riley & Scarborough LLP; Anthony A. Laurentano; Jeanne M. DiGiorgio, Esq.

(57) ABSTRACT

Iguratimod, Repirinast, Lobenzarit, Actarit, Ifenprodil, Bemithyl, Bromantane, Emoxypine, Udenafil, and/or Istradefylline are used for the treatment or prophylaxis of renal fibrosis, kidney disease, or chronic kidney disease in a subject.

8 Claims, 13 Drawing Sheets

(56) References Cited

OTHER PUBLICATIONS

Fouad et al., Pharmacology 2010, vol. 85, pp. 158-167. (Year: 2010).*

Tong et al., Kidney Blood Press Res 2016, vol. 41, pp. 335-344. (Year: 2016).*

Advances in Immunopharmacology Proceeding of the Fourth International Conference on Immunopharmacology, Osaka, Japan, May 16-19, 1988 1st Edition—Apr. 1, 1989, pp. 289-290. Editor: J. W. Hadden (Year: 1989).*

Patel et al., J Allergy Clin Immunol, 1992, vol. 90(5), pp. 782-788. (Year: 1992).*

Agrawal et al., "Effect of telmisartan on kidney function in patients with chronic kidney disease: an observational study", J. Drug. Assess. 2016; 5(1):24-28.

Eddy et al., "Investigating mechanisms of chronic kidney disease in mouse models", Pediatr Nephrol. Aug. 2012; 27(8):1233-1247.

Grande et al., "Fibroblast activation and myofibroblast generation in obstructive nephropathy", Nat Rev Nephrol., Jun. 2009; 5(6):319-328.

International Preliminary Report on Patentability, PCT/CA2019/050881, dated Jan. 7, 2021, 8 Pages.

International Search Report and Written Opinion, PCT/CA2019/050881, dated Sep. 4, 2019, 11 pages.

Arozal, W et al., "Telmisartan prevents the progression of renal injury in daunorubicin rats with the alteration of angiotensin II and endothelin-1 receptor expression associated with its PPAR-gamma agonist actions," Toxicology, vol. 279(1-3): 91-99 (2011).

Nagase, Michiko et al. "Isoamyl 5, 6-dihydro-7, 8-dimethyl-4, 5-dioxo-4H-pyrano[3, 2-c]quinoline-2-carboxylate (MY-5116)," Drugs Research, vol. 17(3): 545-559 (1986).

Legere, S. et al., "Mast Cells in Cardiac Fibrosis: New Insights Suggest Opportunities for Intervention," Front Immunol., 10 pages (2019).

Wilgus, T. et al., "A Review of the Evidence for and against a Role for Mast Cells in Cutaneous Scarring and Fibrosis," Int J Mol Sci., vol. 21(24):9673, 21 pages (2020).

Akula S, et al., "Quantitative In-Depth Analysis of the Mouse Mast Cell Transcriptome Reveals Organ-Specific Mast Cell Heterogeneity," Cells, vol. 9(1):211(2020) . doi: 10.3390/cells9010211. PMID: 31947690; PMCID: PMC7016716.

Cildir G. et al., "The transcriptional program, functional heterogeneity, and clinical targeting of mast cells," J Exp Med., vol. 214(9):2491-2506 (2017) doi: 10.1084/jem.20170910. Epub Aug. 15, 2017. PMID: 28811324; PMCID: PMC5584128.

Crivellato E, et al., "The mast cell: an active participant or an innocent bystander?," Histol Histopathol., vol. 19 (1):259-70 (2004). doi: 10.14670/HH-19.259. PMID: 14702194.

Dwyer DF. et al., "Immunological Genome Project Consortium. Expression profiling of constitutive mast cells reveals a unique identity within the immune system," Nat Immunol., vol. 17(7): 878-87 (2016) . doi: 10.1038/ni.3445. Epub May 2, 2016. PMID: 27135604; PMCID: PMC5045264.

Frossi B, et al., "Is it time for a new classification of mast cells? What do we know about mast cell heterogeneity?," Immunol Rev. vol. 282(1):35-46 (2018) doi: 10.1111/imr.12636. PMID: 29431204.

Moon TC, et al., "Advances in mast cell biology: new understanding of heterogeneity and function," Mucosal Immunol., vol. 3(2):111-28 (2010) doi: 10.1038/mi.2009.136. Epub Dec. 30, 2009. PMID: 20043008.

Sinniah A. et al., "The Anti-allergic Cromones: Past, Present, and Future," Front Pharmacol., vol. 8 (827) 10 pages (2017). doi: 10.3389/fphar.2017.00827. PMID: 29184504; PMCID: PMC5694476.

Varricchi G., et al., "Human mast cells and basophils-How are they similar how are they different?," Immunol Rev., vol. 282(1):8-34 (2018) doi: 10.1111/imr.12627. PMID: 29431214.

West PW et al., "Mast cell tissue heterogeneity and specificity of immune cell recruitment," Front Immunol., vol. 13 (2022):932090. doi: 10.3389/fimmu.2022.932090. PMID: 35967445; PMCID: PMC9374002.

* cited by examiner

USE OF REPIRINAST IN THE PROPHYLAXIS OR TREATMENT OF RENAL FIBROSIS OR KIDNEY DISEASE

REFERENCE TO RELATED APPLICATIONS

This application is a 35 U.S.C. 371 national stage filing of International Application No. PCT/CA2019/050881, filed on Jun. 25, 2019, which claims priority to U.S. provisional application No. 62/690,738 filed Jun. 27, 2018 and U.S. provisional application No. 62/809,330 filed Feb. 22, 2019, the contents of which are hereby incorporated by reference.

FIELD OF INVENTION

The present invention relates to the use of compounds for treating kidney disorders, and in particular, the use of particular compounds for treating renal fibrosis and/or chronic kidney disease.

BACKGROUND

Chronic kidney disease (CKD) is a form of kidney disease characterized by damage to the kidneys that worsens over time, often as result of renal fibrosis. This causes gradual loss of kidney functions, so that excess fluid and waste from the blood remain in the body and may cause other health problems.

Early on, an individual with CKD is generally asymptomatic. As the disease progresses, however, symptoms can include muscle cramps, nausea and vomiting, loss of appetite, swelling in your feet and ankles, and tiredness. Symptoms of acute kidney failure include abdominal and back pain, diarrhea, vomiting, and fever.

Factors which increase the risk of CKD include diabetes, high blood pressure, heart disease, advanced age and a family history of the condition. Blood tests checking for glomerular filtration rate and urine tests to check for albumin (albumin being a protein that can pass into the urine when the kidneys are damaged) can be used to diagnose CKD.

There is currently no cure for renal fibrosis or CKD. Treatment of CKD generally focus on controlling the risk factors, the goal of therapy is simply to slow down or halt the progression of CKD.

The murine model of UUO surgical intervention is a well-characterized experimental model of renal injury that ultimately leads to tubulointerstitial fibrosis, depending on the duration of obstruction. In this model, the progression of renal fibrosis is highly predictable and reproducible, leading to significant fibrosis and nephron loss in a relatively short period of 7 to 14 days (Eddy et al., *Investigating mechanisms of chronic kidney disease in mouse models, Pediatr Nephrol.* 2012 August; 27(8):1233-47; Grande M T and Lopez-Novoa J M, *Fibroblast activation and myofibroblast generation in obstructive nephropathy, Nat Rev Nephrol.,* 2009 June; 5(6):319-28).

Telmisartan is an angiotensin receptor blockcer used to treat hypertension. It is the lead candidate studied for treatment of chronic kidney disease (Agrawal et al., *J. Drug. Assess.* 2016; 5(1):24-28).

The present invention provides a novel use of existing drugs, typically studied as potential therapies for other pathologies, for the treatment and/or alleviation of renal fibrosis and chronic kidney disease.

SUMMARY OF INVENTION

In another embodiment, the present invention provides methods and uses of Iguratimod in the prophylaxis or treatment of renal fibrosis or kidney disease in a subject.

In another embodiment, the present invention provides methods and uses of Repirinast in the prophylaxis or treatment of renal fibrosis or kidney disease in a subject.

In another embodiment, the present invention provides methods and uses of Lobenzarit in the prophylaxis or treatment of renal fibrosis or kidney disease in a subject.

In another embodiment, the present invention provides methods and uses of Actarit in the prophylaxis or treatment of renal fibrosis or kidney disease in a subject.

In another embodiment, the present invention provides methods and uses of Ifenprodil in the prophylaxis or treatment of renal fibrosis or kidney disease in a subject.

In another embodiment, the present invention provides methods and uses of Bemithyl in the prophylaxis or treatment of renal fibrosis or kidney disease in a subject.

In another embodiment, the present invention provides methods and uses of Bromantane in the prophylaxis or treatment of renal fibrosis or kidney disease in a subject.

In another embodiment, the present invention provides methods and uses of Emoxypine in the prophylaxis or treatment of renal fibrosis or kidney disease in a subject.

In another embodiment, the present invention provides methods and uses of Udenafil in the prophylaxis or treatment of renal fibrosis or kidney disease in a subject.

In another embodiment, the present invention provides methods and uses of Istradefylline in the prophylaxis or treatment of renal fibrosis or kidney disease in a subject.

In a further aspect, the kidney disease is chronic kidney disease.

BRIEF DESCRIPTION OF THE FIGURES

Exemplary embodiments are illustrated in referenced figures of the drawings. It is intended that the embodiments and figures disclosed herein are to be considered illustrative rather than restrictive.

DETAILED DESCRIPTION

Figure 1:
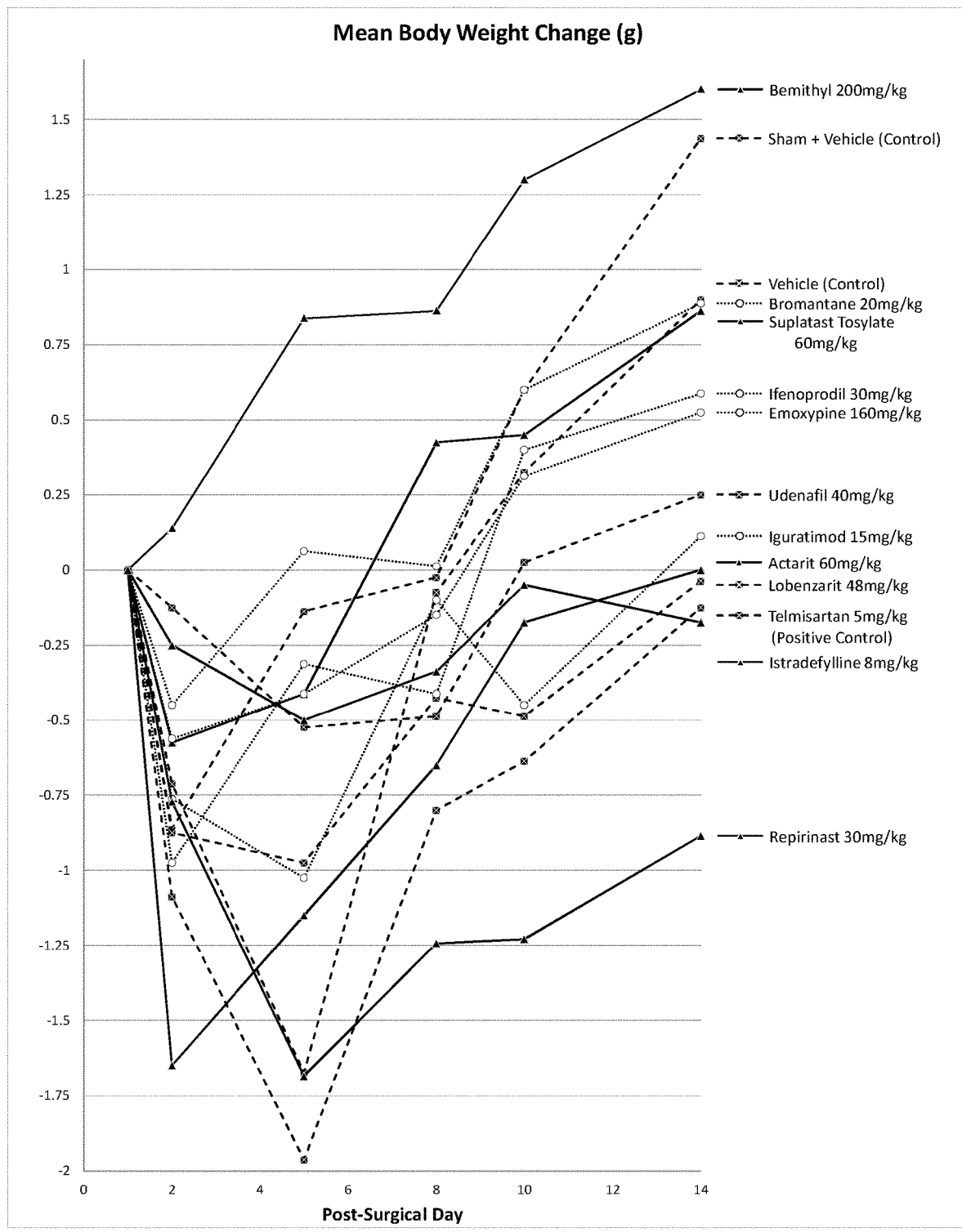
FIG. 1 shows a comparison of the change in mean body weight in grams for each of the 14 study groups of C57BL/6 mice a first example consisting of the sham surgery control group "Sham+Vehicle (Control)", the surgery vehicle control group "Vehicle (Control)", and the 12 treatment groups including the positive control treatment group, Telmisartan.

The inventor has found that a number of pharmacologic compounds approved for use in other pathologies are useful in inhibiting renal fibrosis and may be useful in the prophylaxis and/or treatment of kidney disease. In some embodiments, it is found that in the murine model of UUO surgical intervention, the level of fibrosis is inhibited or alleviated. Based on the experimental results described herein, it is shown that the compounds described herein will be useful in some embodiments in the prophylaxis and/or treatment of kidney disease and chronic kidney disease.

The examples and data below show the effects of inhibiting or alleviating renal fibrosis using test compounds in two studies. In the first study, a therapeutically effective amount of 11 pharmacologic compounds was administered. In the second study, a therapeutically effective amount of 4 pharmacologic compounds were administered, some in combination with Telmisartan. The pharmacologic compounds, hereinafter known as "test agents", are approved for use in other pathologies, and are formulated with a pharmaceutically acceptable vehicle for the purpose of delivery and absorption.

The current standard for treating kidney disease is administering the pharmacologic compound Telmisartan, which was used as a positive control in the experimental examples described herein.

Telmisartan, 2-(4-{[4-Methyl-6-(1-methyl-1H-1,3-benzodiazol-2-yl)-2-propyl-1H-1,3-benzodiazol-1-yl]methyl}phenyl)benzoic acid, is an angiotensin receptor blocker known in the art for treating hypertension. The chemical structure of Telmisartan is as follows:

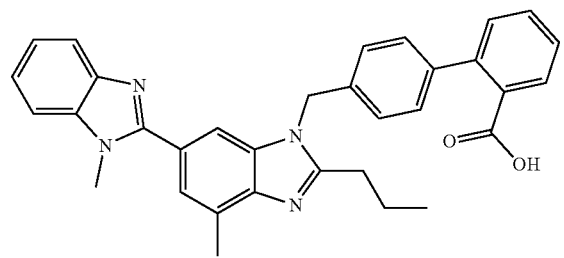 [SMILES: CCCc1nc2c(C)cc(-c3nc4ccccc4n3C)cc2n1Cc1ccc(-c2ccccc2C(=O)O)cc1]

Use of Iguratimod

Iguratimod, N-(7-(Methylsulfonamido)-4-oxo-6-phenoxy-4H-chromen-3-yl)formamide, is known in the art as an anti-inflammatory small molecule drug, often used in the treatment of rheumatoid arthritis. The chemical structure of Iguratimod is as follows:

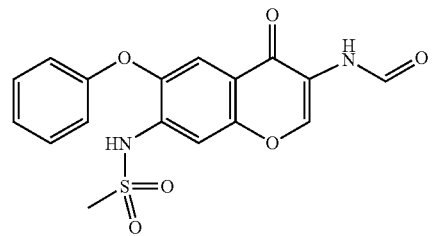 [SMILES: CS(=O)(=O)Nc1cc2occ(NC=O)c(=O)c2cc1Oc1ccccc1]

In one aspect, the present invention provides a use and method of treatment or prophylaxis of renal fibrosis or kidney disease in a subject with Iguratimod or a pharmaceutically acceptable variation thereof. The kidney disease may be chronic kidney disease.

In an embodiment, the amount of Iguratimod used is between 0.4 to 2 mg per kg of the subject per day. In a preferred embodiment, the amount of Iguratimod used is between 0.4 to 0.8 mg per kg of the subject per day (Xiao F, Zhang F, Zhang L L, Wei W (2018) A randomized phase I study to evaluate the safety, tolerability, pharmacokinetics and food-effect of Iguratimod in healthy adult volunteers. Eur J Clin Pharmacol; 74(1):69-77). In a yet further preferred embodiment, the amount of Iguratimod used is about 1.25 mg per kg of the subject per day.

The Iguratimod, or pharmaceutically acceptable variation thereof, may be administered to the subject orally, intravenously or in a manner known in the art. The Iguratimod, or pharmaceutically acceptable variation thereof, may also be administered with one or more pharmaceutically acceptable excipients.

Use of Repirinast

Repirinast, 3-methylbutyl 7,8-dimethyl-4,5-dioxo-5,6-dihydro-4H-pyrano[3,2-c]quinoline-2-carboxylate, is known in the art as an antihistamine. The chemical structure of Repirinast is as follows:

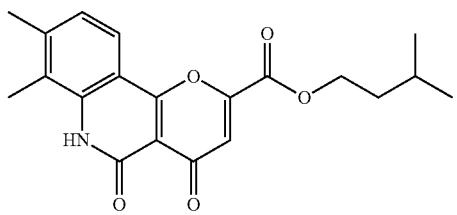 [SMILES: Cc1ccc2c([nH]c(=O)c3c(=O)cc(C(=O)OCCC(C)C)oc32)c1C]

In one aspect, the present invention provides a use and method of treatment or prophylaxis of renal fibrosis or kidney disease in a subject with Repirinast or a pharmaceutically acceptable variation thereof. The kidney disease may be chronic kidney disease.

In an embodiment, the amount of Repirinast used is between 0.5 to 25 mg per kg of the subject. In a preferred embodiment, the amount of Repirinast used is between 1 to 5 mg per kg of the subject. In a further preferred embodiment, the amount of Repirinast used is about 2.5 mg per kg of the subject. In a further preferred embodiment, the amount of Repirinast used is about 7.5 mg per kg of the subject.

In combination with the above Repirinast embodiments, the present invention also provides a use and method of treatment or prophylaxis of renal fibrosis or kidney disease in the subject with Telmisartan. In an embodiment, the amount of Telmisartan used in combination with the Repirinast is between 0.1 to 5 mg per kg of the subject. In a preferred embodiment, the amount of Telmisartan used in combination with the Repirinast is between 0.1 to 1 mg per kg of the subject. In a further preferred embodiment, the amount of Telmisartan used in combination with the Repirinast is about 0.25 mg per kg of the subject.

In another embodiment, the amount of Repirinast used is between 75 to 105 mg per kg of the subject. In a preferred embodiment, the amount of Repirinast used is between 80 to 100 mg per kg of the subject. In another preferred embodiment, the amount of Repirinast used is between 85 to 95 mg per kg of the subject. In a further preferred embodiment, the amount of Repirinast used is about 90 mg per kg of the subject.

The Repirinast, or pharmaceutically acceptable variation thereof, along with the Telmisartan, may be administered to the subject orally, intravenously or in a manner known in the art. The Repirinast, or pharmaceutically acceptable variation thereof, along with the Telmisartan may also be administered with one or more pharmaceutically acceptable excipients.

Use of Lobenzarit

Lobenzarit, 2-[(2-Carboxyphenyl)amino]-4-chlorobenzoic acid, is an immunomodulator known in the art for treatment of arthritis. The chemical structure of Lobenzarit is as follows:

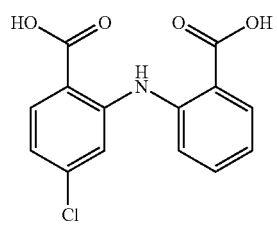 [SMILES: O=C(O)c1ccccc1Nc1cc(Cl)ccc1C(=O)O]

In one aspect, the present invention provides a use and method of treatment or prophylaxis of renal fibrosis or kidney disease in a subject with Lobenzarit or a pharmaceutically acceptable variation thereof. The kidney disease may be chronic kidney disease.

In an embodiment, the amount of Lobenzarit used is between 1 to 20 mg per kg of the subject. In a preferred embodiment, the amount of Lobenzarit used is between 2 to 15 mg per kg of the subject. In another preferred embodiment, the amount of Lobenzarit used is between 3 to 10 mg per kg of the subject. In a yet further preferred embodiment, the amount of Lobenzarit used is about 4 mg per kg of the subject.

The Lobenzarit, or pharmaceutically acceptable variation thereof, may be administered to the subject orally, intravenously or in a manner known in the art. The Lobenzarit, or pharmaceutically acceptable variation thereof, may also be administered with one or more pharmaceutically acceptable excipients.

Use of Actarit

Actarit, (4-Acetamidophenyl)acetic acid, is a disease-modifying antirheumatic drug known in the art for treatment of rheumatoid arthritis. The chemical structure of Actarit is as follows:

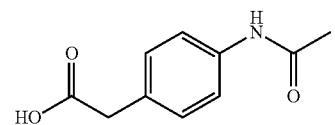

In one aspect, the present invention provides a use and method of treatment or prophylaxis of renal fibrosis or kidney disease in a subject with Actarit or a pharmaceutically acceptable variation thereof. The kidney disease may be chronic kidney disease.

In an embodiment, the amount of Actarit used is between 1 to 20 mg per kg of the subject. In a preferred embodiment, the amount of Actarit used is between 2 to 10 mg per kg of the subject. In another preferred embodiment, the amount of Actarit used is between 3 to 8 mg per kg of the subject. In a yet further preferred embodiment, the amount of Actarit used is about 5 mg per kg of the subject.

The Actarit, or pharmaceutically acceptable variation thereof, may be administered to the subject orally, intravenously or in a manner known in the art. The Actarit, or pharmaceutically acceptable variation thereof, may also be administered with one or more pharmaceutically acceptable excipients.

Use of Ifenprodil

Ifenprodil, 4-[2-(4-benzylpiperidin-1-ium-1-yl)-1-hydroxypropyl]phenol; 2,3,4-trihydroxy-4-oxobutanoate, is known in the art as a selective NMDA receptor (glutamate) antagonist. Ifenprodil was originally (in the early 1970's)

developed as a vasodilator. Ifenprodil is currently being studied for treatment of adolescent PTSD. The chemical structure is as follows:

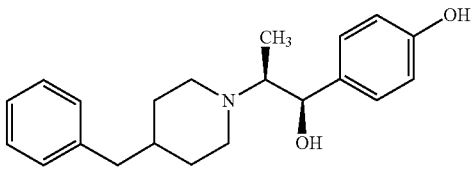 [SMILES: C[C@@H]([C@H](O)c1ccc(O)cc1)N1CCC(Cc2ccccc2)CC1]

In one aspect, the present invention provides a use and method of treatment or prophylaxis of renal fibrosis or kidney disease in a subject with Ifenprodil or a pharmaceutically acceptable variation thereof. The kidney disease may be chronic kidney disease.

In a preferred embodiment, the amount of Ifenprodil used is between 0.2 and 20 mg per kg, preferably between 0.5 to 10 mg per kg of the subject. In a further preferred embodiment, the amount of Ifenprodil used is between 1 to 5 mg per kg of the subject. In a still further preferred embodiment, the amount of Ifenprodil used is abut 1 mg per kg of the subject.

The Ifenprodil, or pharmaceutically acceptable variation thereof, may be administered to the subject orally, intravenously or in a manner known in the art. The Ifenprodil, or pharmaceutically acceptable variation thereof, may also be administered with one or more pharmaceutically acceptable excipients.

Use of Bemithyl

Bemithyl, 2-Ethylsulfanyl-1H-benzoimidazole, is known in the art as a synthetic actoprotector, antioxidant, and antimutagenic, and is often used to increase physical performance. The chemical structure of Bemithyl is as follows:

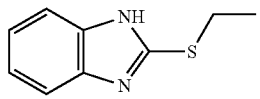

In one aspect, the present invention provides a use and method of treatment or prophylaxis of renal fibrosis or kidney disease in a subject with Bemithyl or a pharmaceutically acceptable variation thereof. The kidney disease may be chronic kidney disease.

In an embodiment, the amount of Bemithyl used is between 1 to 80 mg per kg of the subject. In a preferred embodiment, the amount of Bemithyl used is between 5 to 50 mg per kg of the subject. In a further preferred embodiment, the amount of Bemithyl used is between 10 to 30 mg per kg of the subject. In a yet further preferred embodiment, the amount of Bemithyl used is between 15 to 20 mg per kg of the subject. In a still further preferred embodiment, the amount of Bemithyl used is about 17 mg per kg of the subject.

In combination with the above Bemithyl embodiments, the present invention also provides a use and method of treatment or prophylaxis of renal fibrosis or kidney disease in the subject with Telmisartan. In an embodiment, the amount of Telmisartan used in combination with the Bemithyl is between 0.1 to 2 mg per kg of the subject. In a preferred embodiment, the amount of Telmisartan used in combination with the Bemithyl is between 0.1 to 0.5 mg per kg of the subject. In a further preferred embodiment, the amount of Telmisartan used in combination with the Bemithyl is about 0.25 mg per kg of the subject.

The Bemithyl, or pharmaceutically acceptable variation thereof, along with the Telmisartan may be administered to the subject orally, intravenously or in a manner known in the art. The Bemithyl, or pharmaceutically acceptable variation thereof, along with the Telmisartan may also be administered with one or more pharmaceutically acceptable excipients.

Use of Bromantane

Bromantane, N-(4-Bromophenyl)adamantan-2-amine, is an atypical psychostimulant and anxiolytic drug of the adamantine family known in the art of treatment of neurasthenia. The chemical structure of Bromantane is as follows:

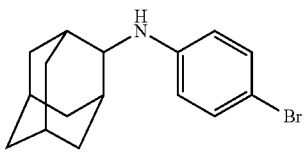 [SMILES: Brc1ccc(NC2C3CC4CC(C3)CC2C4)cc1]

In one aspect, the present invention provides a use and method of treatment or prophylaxis of renal fibrosis or kidney disease in a subject with Bromantane or a pharmaceutically acceptable variation thereof. The kidney disease may be chronic kidney disease.

In an embodiment, the amount of Bromantane used is between 0.5 to 10 mg per kg of the subject. In a preferred embodiment, the amount of Bromantane used is between 1 to 3 mg per kg of the subject. In a preferred embodiment, the amount of Bromantane used is between 1.7 to 3.3 mg per kg of the subject. In a further preferred embodiment, the amount of Bromantane used is about 2.5 mg per kg of the subject.

The Bromantane, or pharmaceutically acceptable variation thereof, may be administered to the subject orally, intravenously or in a manner known in the art. The Bromantane, or pharmaceutically acceptable variation thereof, may also be administered with one or more pharmaceutically acceptable excipients.

Use of Emoxypine Emoxypine, 2-Ethyl-6-methyl-3-hydroxypyridine, is known in the art as an antioxidant. The chemical structure of Emoxypine is as follows:

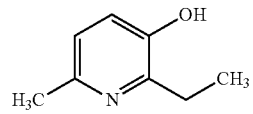

In one aspect, the present invention provides a use and method of treatment or prophylaxis of renal fibrosis or kidney disease in a subject with Emoxypine or a pharmaceutically acceptable variation thereof. The kidney disease may be chronic kidney disease.

In an embodiment, the amount of Emoxypine used is between 1 to 50 mg per kg of the subject. In a further preferred embodiment, the amount of Emoxypine used is between 5 to 30 mg per kg of the subject. In a yet further preferred embodiment, the amount of Emoxypine used is between 10 to 20 mg per kg of the subject. In a still further preferred embodiment, the amount of Emoxypine used is about 13 mg per kg of the subject.

The Emoxypine, or pharmaceutically acceptable salt thereof, may be administered to the subject orally, intravenously or in a manner known in the art. The Emoxypine, or pharmaceutically acceptable salt thereof, may also be administered with one or more pharmaceutically acceptable excipients.

Use of Udenafil

Udenafil, $C_{25}H_{36}N_6O_4S$, is an phosphodiesterase type 5 (PDE5) inhibitor used to treat erectile dysfunction. The chemical structure of Udenafil is as follows:

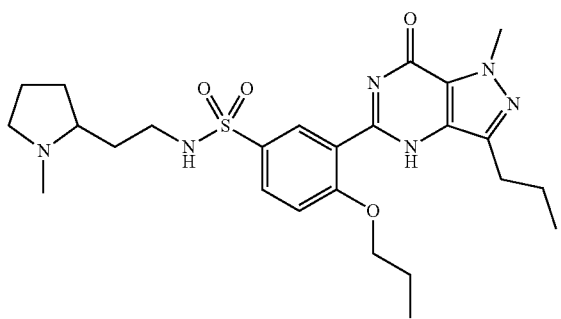 [SMILES: CCCOc1ccc(S(=O)(=O)NCCC2CCCN2C)cc1-c1nc(=O)c2c([nH]1)c(CCC)nn2C]

In one aspect, the present invention provides a use and method of treatment or prophylaxis of renal fibrosis or kidney disease in a subject with Udenafil or a pharmaceutically acceptable variation thereof. The kidney disease may be chronic kidney disease.

In an embodiment, the amount of Udenafil used is between 1 to 10 mg per kg of the subject. In a preferred embodiment, the amount of Udenafil used is between 2 to 5 mg per kg of the subject. In a preferred embodiment, the amount of Udenafil used is between 1.7 to 3.3 mg per kg of the subject. In a further preferred embodiment, the amount of Udenafil used is about 3 mg per kg of the subject.

The Udenafil, or pharmaceutically acceptable variation thereof, may be administered to the subject orally, intravenously or in a manner known in the art. The Udenafil, or pharmaceutically acceptable variation thereof, may also be administered with one or more pharmaceutically acceptable excipients.

Use of Istradefylline

Istradefylline, 8-[(E)-2-(3,4-dimethoxyphenyl)vinyl]-1,3-diethyl-7-methyl-3,7-dihydro-1H-purine-2,6-dione, is a selective A2A receptor antagonist known in the art for treatment of dyskinesia in Parkinson's disease. The chemical structure of Istradefylline is as follows:

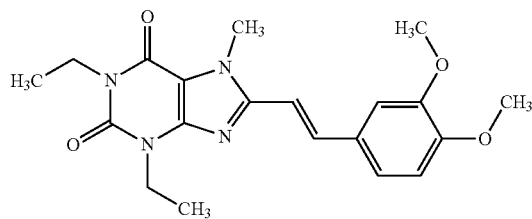 [SMILES: CCn1c(=O)c2c(nc(/C=C/c3ccc(OC)c(OC)c3)n2C)n(CC)c1=O]

In one aspect, the present invention provides a use and method of treatment or prophylaxis of renal fibrosis or kidney disease in a subject with Istradefylline or a pharmaceutically acceptable variation thereof. The kidney disease may be chronic kidney disease.

In an embodiment, the amount of Istradefylline used is between 0.2 to 5 mg per kg of the subject. In a preferred embodiment, the amount of Istradefylline used is between 0.3 to 1.3 mg per kg of the subject. In a further preferred embodiment, the amount of Istradefylline used is about 0.7 mg per kg of the subject.

The Istradefylline, or pharmaceutically acceptable variation thereof, may be administered to the subject orally, intravenously or in a manner known in the art. The Istradefylline, or pharmaceutically acceptable variation thereof, may also be administered with one or more pharmaceutically acceptable excipients.

Use of Suplatast Tosylate

Suplatast Tosylate, (3-{[4-(3-ethoxy-2-hydroxypropoxy)phenyl]amino}-3-oxopropyl)(dimethyl)sulfonium 4-methylbenzenesulfonate, is a Th2 cytokine inhibitor known in the art as an antiallergic agent. The chemical structure of Suplatast Tosylate is as follows:

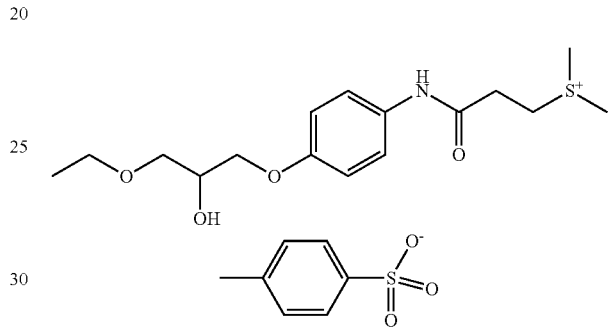

In one aspect, the present invention provides a use and method of treatment or prophylaxis of renal fibrosis or kidney disease in a subject with Suplatast Tosylate or a pharmaceutically acceptable salt thereof. The kidney disease may be chronic kidney disease.

In a preferred embodiment, the amount of Suplatast Tosylate used is between 1 to 20 mg per kg of the subject. In another preferred embodiment, the amount of Suplatast Tosylate used is between 2 to 10 mg per kg of the subject. In a yet further preferred embodiment, the amount of Suplatast Tosylate used is about 5 mg per kg of the subject.

The Suplatast Tosylate, or pharmaceutically acceptable salt thereof, may be administered to the subject orally, intravenously or in a manner known in the art. The Suplatast Tosylate, or pharmaceutically acceptable salt thereof, may also be administered with one or more pharmaceutically acceptable excipients.

Use in Combination

In another aspect, the present invention provides a use and method of treatment or prophylaxis of chronic kidney disease in a subject with one or more of Iguratimod, Repirinast, Lobenzarit, Actarit, Ifenprodil, Bemithyl, Bromantane, Emoxypine, Udenafil, Istradefyllne, and Suplatast Tosylate, in combination. In another aspect, the present invention provides a use and method of treatment or prophylaxis of chronic kidney disease in a subject with one or more of Iguratimod, Repirinast, Lobenzarit, Actarit, Ifenprodil, Bemithyl, Bromantane, Emoxypine, Udenafil, Istradefyllne, Suplatast Tosylate, and in combination with one or more of Cenicriviroc, telmisartan, a cholesterol lowering drug, an antihypertension drug, or erythropoietin.

Examples of cholesterol lowering drugs for use in combinations include Atorvastatin (Lipitor), Fluvastatin (Lescol), Lovastatin, Pitavastatin (Livalo), Pravastatin (Pravachol), Rosuvastatin calcium (Crestor), Simvastatin (Zocor) and niacin, Alirocumab (Praluent), Evolocumab (Repatha), Alirocumab (Praluent), and Evolocumab (Repatha). Examples of antihypertension drugs for use in combinations include antihypertensives, calcium channel blockers, ACE inhibitors angiotensin II receptor blockers, diuretics, and beta blockers. Examples of known angiotensin II receptor antagonists include both angiotensin I receptor subtype antagonists and angiotensin II receptor subtype antagonists. Suitable antiotensin II receptor antagonists include losartan and valsartan. Suitable calcium channel blockers include, for example, verapamil, diltiazem, nicardipine, nifedipine, amlodipine, felodipine, nimodipine, and bepridil. Diuretics include, for example, furosemide, diuril, amiloride, and hydrodiuril. Losartan, candesartan, telmisartan, valsartan, olmesartan, irbesartan, and the like can be used as a hypotensive agent.

The term "effective amount" used herein refers to the amount of an active ingredient sufficient to confer a desired prophylactic or therapeutic effect in a treated subject. In one aspect, an effective amount for inhibiting or alleviating hepatic steatosis, lobular inflammation, hepatocellular ballooning or NASH-derived HCC improves or reduces one or more symptoms, conditions or progression thereof. In some embodiments, the symptoms, conditions or progression are determined and evaluated using methods known in the art that measure various disease progress-related indexes, for example by analyzing liver sections via immunohistochemical staining. In some embodiments, the effective amount is determined by persons skilled in the art evaluating, for example, the administration route and frequency, body weight and species of the subject receiving the pharmacologic compound. In some embodiments, an effective amount of the pharmacologic compound is formulated with a pharmaceutically acceptable vehicle and administered to the subject.

The term "pharmaceutically acceptable" used herein means that the vehicle is known in the art as compatible with the pharmacologic compound while also being safe to the subject receiving the treatment. In some embodiments, the pharmaceutically acceptable vehicle is determined by persons skilled in the art evaluating, for example, the solubility of the pharmacologic compound in said vehicle.

Exemplary embodiments of the present invention are further described with reference to the following examples, which are intended to be illustrative and not limiting in nature. In the first study, a therapeutically effective amount of 10 pharmacologic compounds was administered. In the second study, a therapeutically effective amount of 4 pharmacologic compounds were administered, some in combination with administration of Telmisartan.

Example 1

Materials and Methods

Male 9-12 week old C57BL/6 mice of 23-25 grams body weight were used. All mice were acclimated for a minimum of 5 days prior to the start of the study and housed individually in microisolators throughout the study in a 12:12 light-dark cycle on a standard maintenance mouse chow diet (Harlan Teklad 2018) with food and water given ad libitum. Prior to surgery, all mice were weighed for baseline body weight.

The UUO surgical intervention was performed according to previously described methods known in the art (Le Meur Y et al., *Macrophage accumulation at a site of renal inflammation is dependent on the M-CSF/c-fms pathway, J Leukocyte Biol.*, 72:530-537; 2002).

All mice were first anesthetized by intraperitoneal injection with a rodent cocktail (ketamine 10 mg/mL and Xyaline 1 mg/mL) in normal saline (10 µL/g body weight). Pedal reflex and movement of the vibrissae were used to determine the state of unconsciousness. A state of unconsciousness was confirmed after a period of about 5 minutes in all animals. All mice were then shaved on the left side of the abdomen. The shaved area was first swabbed with iodine and then swabbed with alcohol. A vertical incision was made through the skin with a #22 scalpel and the skin was then retracted. A further incision of about 2.5 cm was then made through the peritoneum avoiding any major blood vessels. The peritoneum was then retracted and the left kidney was exposed.

The left kidney was then brought to the surface by hooking the ureter directly beneath the kidney with sterile forceps and gently manipulating the kidney upward. The ureter was ligated at two points directly below the kidney with 5-0 surgical silk with excess suture cut away and discarded post-ligation. The kidney was then gently placed back to its correct anatomical position and the abdomen was lavaged with 1 mL sterile saline to replenish fluid loss. The peritoneum and then skin were sutured with 5-0 Mersilene, and the incision site was gently wiped with iodine. All mice were then placed individually in clean cages that were set on top of a thermal blanket until recovery at about 30-60 minutes later. In some examples, sham surgery was performed as a control by following all steps of the UUO surgical intervention procedure except ligation.

Following surgery, the mice were divided into 14 individual study groups of 8 mice each and, following post-surgical recovery, administered a once-daily oral treatment for 14 days. The mice in 12 of the 14 study groups (hereafter known as "treatment groups") had all received the UUO surgical ligation and were treated individually with a distinct pharmacologic compound as set out in Table 1. The mice in 2 of the 14 study groups were treated individually with a pharmaceutically acceptable vehicle with no active ingredient. The pharmaceutically acceptable vehicle in all groups was 0.5% carboxymethyl cellulose (CMC). All mice were sacrificed with $CO_2$ on post-surgical day 15.

TABLE 1

| Group | Description | N | ROA | Dose mg/kg | Dosing Volume | Dosing Frequency |
|---|---|---|---|---|---|---|
| 1 | Sham + vehicle (0.5% CMC) | 8 | PO | xxxx | 10 ml/kg | QD Days 1-14 |
| 2 | Surgery + Vehicle | 8 | PO | xxxx | 10 ml/kg | QD Days 1-14 |
| 3 | Surgery + Telmisartan | 8 | PO | 5 | 10 ml/kg | QD Days 1-14 |
| 4 | Surgery + Iguratimod | 8 | PO | 15 | 10 ml/kg | QD Days 1-14 |
| 5 | Surgery + Repirinast | 8 | PO | 30 | 10 ml/kg | QD Days 1-14 |
| 6 | Surgery + Lobenzarit | 8 | PO | 48 | 10 ml/kg | QD Days 1-14 |
| 7 | Surgery + Actarit | 8 | PO | 60 | 10 ml/kg | QD Days 1-14 |
| 8 | Surgery + Ifenprodil | 8 | PO | 30 | 10 ml/kg | QD Days 1-14 |
| 9 | Surgery + Bemithyl | 8 | PO | 200 | 10 ml/kg | QD Days 1-14 |
| 10 | Surgery + Bromantane | 8 | PO | 20 | 10 ml/kg | QD Days 1-14 |
| 11 | Surgery + Emoxypine | 8 | PO | 160 | 10 ml/kg | QD Days 1-14 |

TABLE 1-continued

| Group | Description | N | ROA | Dose mg/kg | Dosing Volume | Dosing Frequency |
|---|---|---|---|---|---|---|
| 12 | Surgery + Udenafil | 8 | PO | 40 | 10 ml/kg | QD Days 1-14 |
| 13 | Surgery + Istradefyllne | 8 | PO | 8 | 10 ml/kg | QD Days 1-14 |
| 14 | Surgery + Suplatast Tosylate | 8 | PO | 60 | 10 ml/kg | QD Days 1-14 |

The dose selected for the animal studies was determined by taking the maximum known human daily dose, dividing by the average weight of an adult (~60-70 kg) to get a human mg/kg dose. Then that number was multiplied by 12 to convert to a mouse dose based on conventional dosing tables. See Nair and Jacob, *J Basic Clin* Pharm March 2016-May 2016, 7(2):27-31.

Thus, working backwards to arrive at a human dose, for example: Emoxypine=160 mg/kg divide 12=13.3 mg/kg.

The following measurements and assessments were taken for each mouse.

Body weight: The body weights were measured on days 1, 2, 5, 8, 10 and 14 using a laboratory balance.

Serum collection: A blood sample was then collected from all mice and plasma analyzed for urea nitrogen and creatinine. Plasma was stored at −80° C. for possible future analysis.

Kidney weight: The UUO was then examined in situ to ensure that the surgical ligation ties remained patent. Both the ligated (UUO) and non-ligated kidneys were removed for analysis. Weights of both kidneys were measured using a laboratory balance.

Histopathology: Formalin-fixed kidney cross-section samples were subjected histopathological scoring with Sirius Red staining, and imaged at a magnification of ×20, using standard techniques. All three sections were stained and evaluated. The analysis was performed by a board-certified veterinarian pathologist. The presence of interstitial damage and severity score was assessed according to the following criteria: 0=normal, 1=light, 2=moderate, 3=severe.

Values are arithmetic means. Comparison between the study group and positive control group was performed using a two-tailed, heteroscedastic (two-sample unequal variance) Student's T-Test. A p-value of <0.05 was considered statistically significant.

Results

Body Weight Evaluation: Results of the evaluation of mean body weight change are shown in FIG. 1 and Table 2. Body weights were measured on post-surgical days 1, 2, 5, 8, 10 and 14 as previously described. The mean body weight change of each study group was calculated using the body weight average of all mice in each study group.

TABLE 2

Mean Body Weight Change Following Surgery (g)

| | Days Post Surgery | | | | | |
|---|---|---|---|---|---|---|
| | 1 | 2 | 5 | 8 | 10 | 14 |
| Sham + Vehicle | 0 | −0.86 | −0.14 | −0.02 | 0.60 | 1.44 |
| Vehicle | 0 | −0.71 | −1.68 | −0.07 | 0.32 | 0.90 |
| Telmisartan 5 mg/kg (Positive Control) | 0 | −1.09 | −1.96 | −0.80 | −0.64 | −0.13 |
| Iguratimod 15 mg/kg | 0 | −0.76 | −1.03 | −0.10 | −0.45 | 0.11 |
| Repirinast 30 mg/kg | 0 | −0.77 | −1.69 | −1.24 | −1.23 | −0.89 |
| Lobenzarit 48 mg/kg | 0 | −0.88 | −0.97 | −0.42 | −0.49 | −0.04 |
| Actarit 60 mg/kg | 0 | −1.65 | −1.15 | −0.65 | −0.18 | 0.00 |
| Ifenoprodil 30 mg/kg | 0 | −0.97 | −0.31 | −0.41 | 0.40 | 0.59 |
| Bemithyl 200 mg/kg | 0 | 0.14 | 0.84 | 0.86 | 1.30 | 1.60 |
| Bromantane 20 mg/kg | 0 | −0.45 | −0.06 | 0.01 | 0.60 | 0.89 |
| Emoxypine 160 mg/kg | 0 | −0.56 | −0.41 | −0.15 | 0.31 | 0.52 |
| Udenafil 40 mg/kg | 0 | −0.12 | −0.52 | −0.49 | 0.03 | 0.25 |
| Suplatast Tosylate 60 mg/kg | 0 | −0.58 | −0.41 | 0.43 | 0.45 | 0.86 |
| Istradefylline 8 mg/kg | 0 | −0.25 | −0.50 | −0.34 | −0.05 | −0.18 |

All study groups showed an initial decrease in mean body weight change followed by an increase in mean body weight change until sacrifice.

The mean body weight change on post-surgical day 14 for all treatment groups except Repirinast and Istradefylline showed a more positive value than the positive control treatment group. As compared to the positive control treatment group (Telmisartan), this indicated a greater decrease in body weight on post-surgical day 14 versus post-surgical day 1 in treatment groups Repirinast and Istradefylline, and a greater increase in body weight in the remaining treatment groups.

The mean body weight change on post-surgical day 14 for treatment groups Suplatast Tosylate Bromantane were comparable to that of the surgery vehicle control group.

The mean body weight change on post-surgical day 14 for the Bemithyl treatment group was even greater than that of the sham surgery control group.

Figure 2:
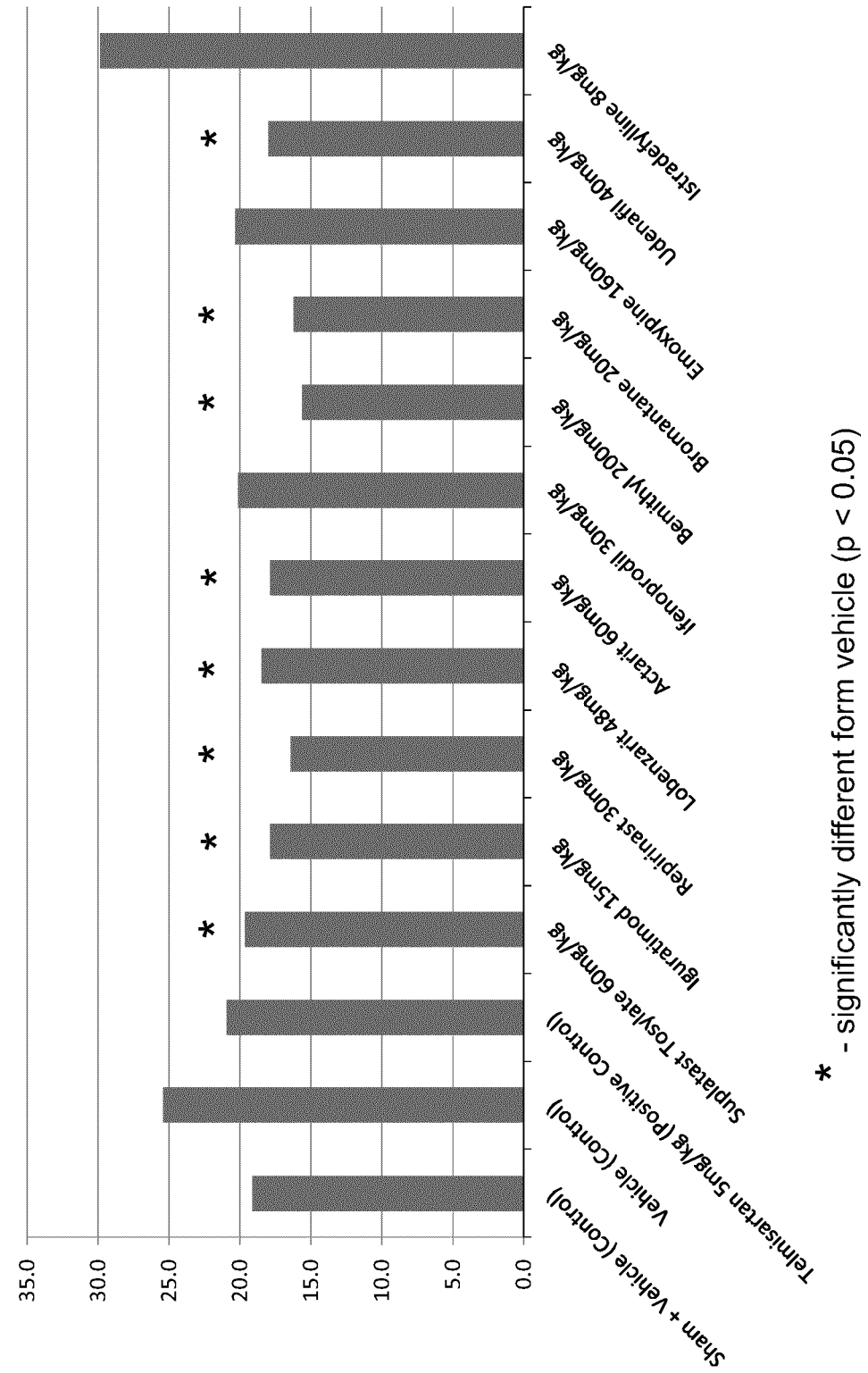
FIG. 2 shows an evaluation of renal function consisting of the plasma urea nitrogen (BUN) in mg/dL for each of the 14 study groups of C57BL/6 mice consisting of the sham surgery control group "Sham+Vehicle (Control)", the surgery vehicle control group "Vehicle (Control)", and the 12 treatment groups including the positive control treatment group.
Figure 3:
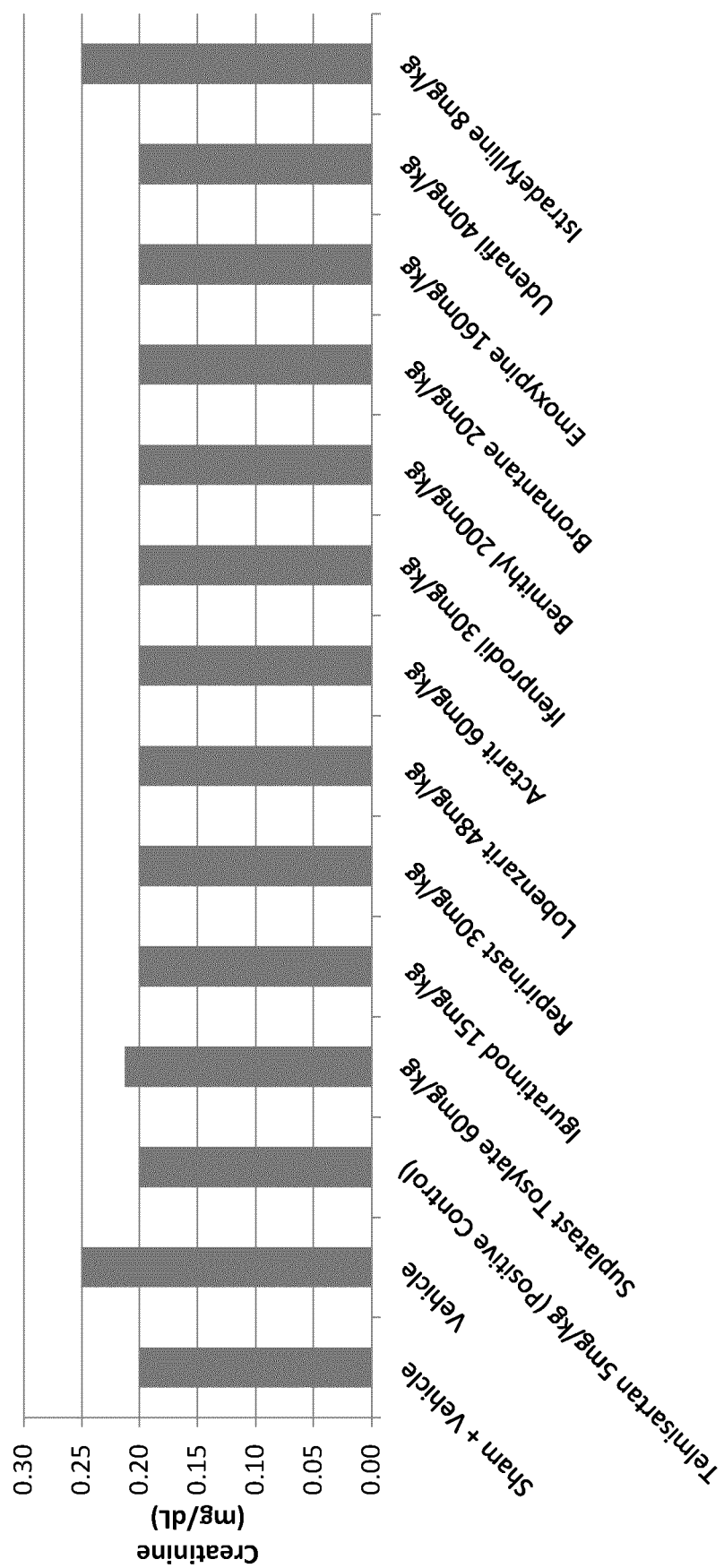
FIG. 3 shows an evaluation of renal function consisting of the Creatinine in mg/dL for each of the 14 study groups of C57BL/6 mice consisting of the sham surgery control group "Sham+Vehicle (Control)", the surgery vehicle control group "Vehicle (Control)", and the 12 treatment groups including the positive control treatment group.

Renal Function Evaluation: Renal function and disease progression was evaluated by BUN (blood urea nitrogen) as previously described. The BUN of each study group consisted of the BUN average of all mice in each study group. Results are shown in FIGS. 2 and 3, and Table 3.

TABLE 3

Results of Renal Function Evaluation.

| Treatment | BUN mg/dL | Creatinine mg/dl |
|---|---|---|
| Sham + Vehicle | 19.125 | 0.20 |
| Vehicle | 25.425 | 0.25 |
| Telmisartan 5 mg/kg (Positive Control) | 20.9 | 0.20 |
| Iguratimod 15 mg/kg | 17.875* | 0.20 |
| Repirinast 30 mg/kg | 16.4*# | 0.20 |
| Lobenzarit 48 mg/kg | 18.4625* | 0.20 |
| Actarit 60 mg/kg | 17.875* | 0.20 |
| Ifenoprodil 30 mg/kg | 20.125 | 0.20 |
| Bemithyl 200 mg/kg | 15.6125*# | 0.20 |
| Bromantane 20 mg/kg | 16.2*# | 0.20 |
| Emoxypine 160 mg/kg | 20.1625 | 0.20 |
| Udenafil 40 mg/kg | 17.9875* | 0.20 |
| Suplatast Tosylate 60 mg/kg | 19.61429* | 0.21 |
| Istradefylline 8 mg/kg | 29.85 | 0.25 |

Note:
Here and in Table 5:
*p <0.05 compared to vehicle (Bonferroni post-test);
p <0.05 compared to vehicle (Tamhane post-test)

The BUN for all treatment groups were decreased in comparison to the surgery vehicle control group except for the Istradefylline treatment group.

The BUN for all treatment groups were decreased in comparison to the positive control treatment group except for the Istradefylline treatment group. This indicated that the treatment groups of Iguratimod, Repirinast, Lobenzarit, Actarit, Ifenoprodil, Bemithyl, Bromantane, Emoxypine and Udenafil had less renal dysfunction and disease progression than the positive control treatment with Telmisartan, the current gold standard for treatment of renal fibrosis.

The BUN for treatment groups Suplatast Tosylate, Iguratimod, Repirinast, Lobenzarit, Actarit, Bemithyl, Bromantane and Udenafil were decreased in comparison to the sham surgery control group. This indicated that treatment with these compounds resulted in an improved renal function as compared to the study group that did not receive any surgical ligation (UUO). Of these compounds, treatment with Bemithyl resulted in the most improved renal function of all.

In particular, Repirinast (30 mg/kg), Bemithyl (200 mg/kg), and Bromantane (20 mg/kg) showed significant reductions in the levels of BUN compared to vehicle ($p<0.05$, Tamhane post-test). When a Bonferroni post-test is applied, significant reductions in BUN are also observed for Suplatast Tosylate (60 mg/kg), Iguratimod (15 mg/kg), Lobenzarit (48 mg/kg), Actarit (60 mg/kg), and Udenafil (40 mg/kg). The positive control, Telmisartan (5 mg/kg), did not show a significant reduction compared to the vehicle. Differences between the test compounds were insignificant. All of the agents tested reduced the levels of serum creatinine compared to vehicle.

Figure 4:
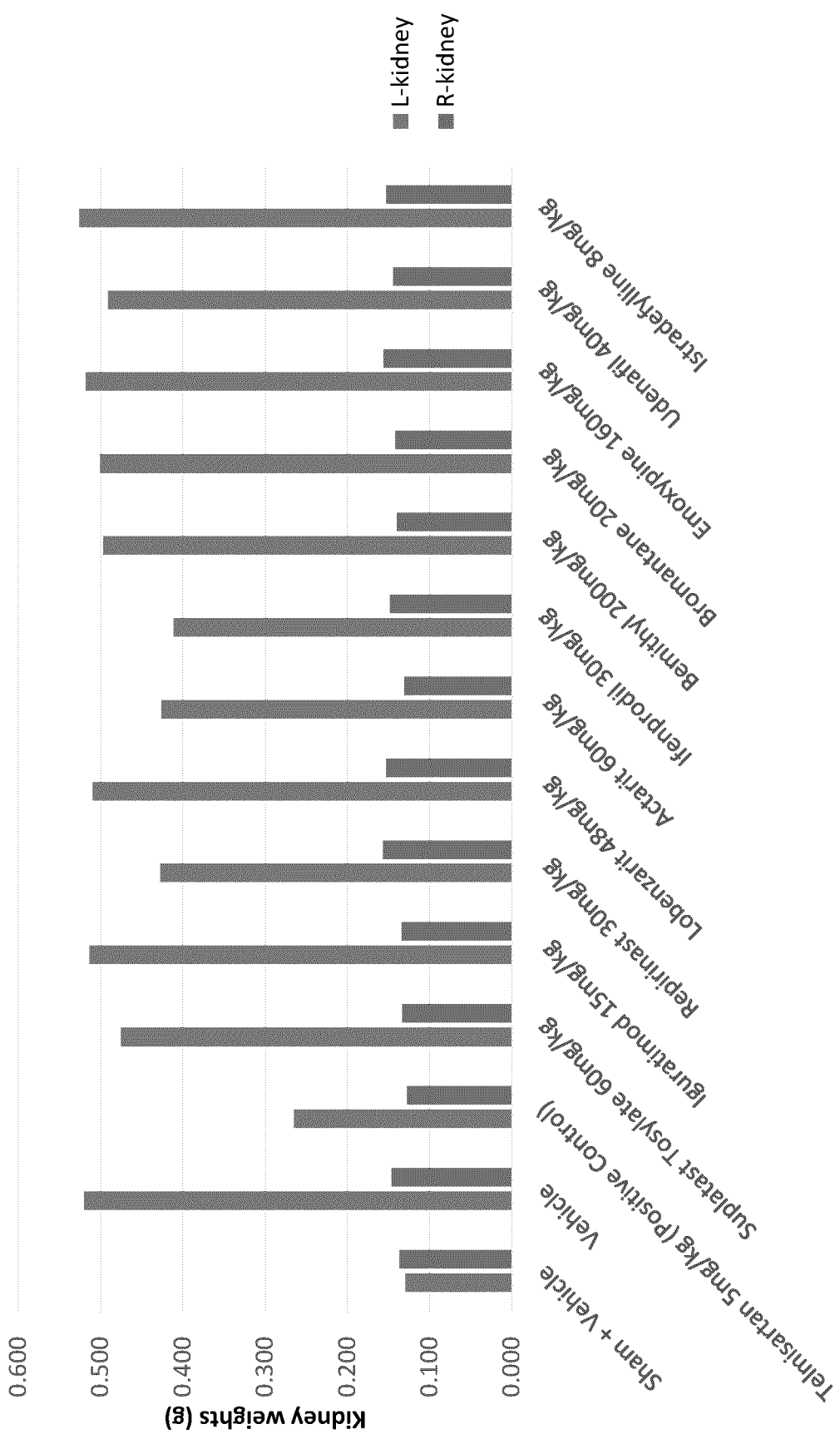
FIG. 4 shows a comparison of the mean weight difference between the left (ligated UUO) and right (non-ligated) kidneys in grams for each of the 14 study groups of C7BL/6 mice consisting of the sham surgery control group "Sham+Vehicle (Control)", the surgery vehicle control group "Vehicle (Control)", and the 12 treatment groups including the positive control treatment group, Telmisartan.

Kidney Weight Evaluation: Kidney weight indicating, which indicates functional and pathological changes in the kidney, was evaluated by measuring the weight of both the ligated (UUO) and non-ligated kidneys as previously described. The ligated and non-ligated kidney weights of each study group consisted of the respective kidney weight averages of all mice in each study group. Results are shown in Table 4 and FIG. 4.

TABLE 4

Kidney Weights for Study Groups.

| | L-kidney | R-kidney | Difference (L – R), g | Reduction |
|---|---|---|---|---|
| Sham + Vehicle | 0.129 | 0.136 | −0.007 | — |
| Vehicle | 0.520 | 0.146 | 0.374 | — |
| Telmisartan 5 mg/kg (Positive Control) | 0.265 | 0.128 | 0.137 | 63% |
| Iguratimod 15 mg/kg | 0.514 | 0.133 | 0.380 | −2% |
| Repirinast 30 mg/kg | 0.427 | 0.157 | 0.270 | 28% |
| Lobenzarit 48 mg/kg | 0.510 | 0.152 | 0.357 | 5% |
| Actarit 60 mg/kg | 0.426 | 0.131 | 0.295 | 21% |
| Suplatast Tosylate 60 mg/kg | 0.475 | 0.133 | 0.342 | 9% |
| Ifenoprodil 30 mg/kg | 0.411 | 0.148 | 0.263 | 30% |
| Bemithyl 200 mg/kg | 0.497 | 0.139 | 0.357 | 5% |
| Bromantane 20 mg/kg | 0.501 | 0.141 | 0.359 | 4% |
| Emoxypine 160 mg/kg | 0.517 | 0.156 | 0.362 | 3% |
| Udenafil 40 mg/kg | 0.491 | 0.144 | 0.347 | 7% |
| Istradefylline 8 mg/kg | 0.526 | 0.153 | 0.373 | 0% |

The ligated kidney weights for all treatment groups and surgery vehicle control group were increased in comparison to the sham surgery control group. The ligated kidney weights for all treatment groups except Istradefylline were increased in comparison to the ligated kidney weight of the positive control treatment group and decreased in comparison to the ligated kidney weight of the surgery vehicle control group. The ligated kidney weight for the Istradefylline treatment group was increased in comparison to the remaining 13 study groups, including the surgery vehicle control group.

The increase in weight of the ligated kidney in comparison to the non-ligated kidney was greater in all treatment groups as compared to the positive control treatment group.

In particular, the positive control Telmisartan (5 mg/kg) showed the greatest numerical reduction in the disparity between the two kidneys. A number of other agents showed smaller reductions in this disparity.

Figure 5:
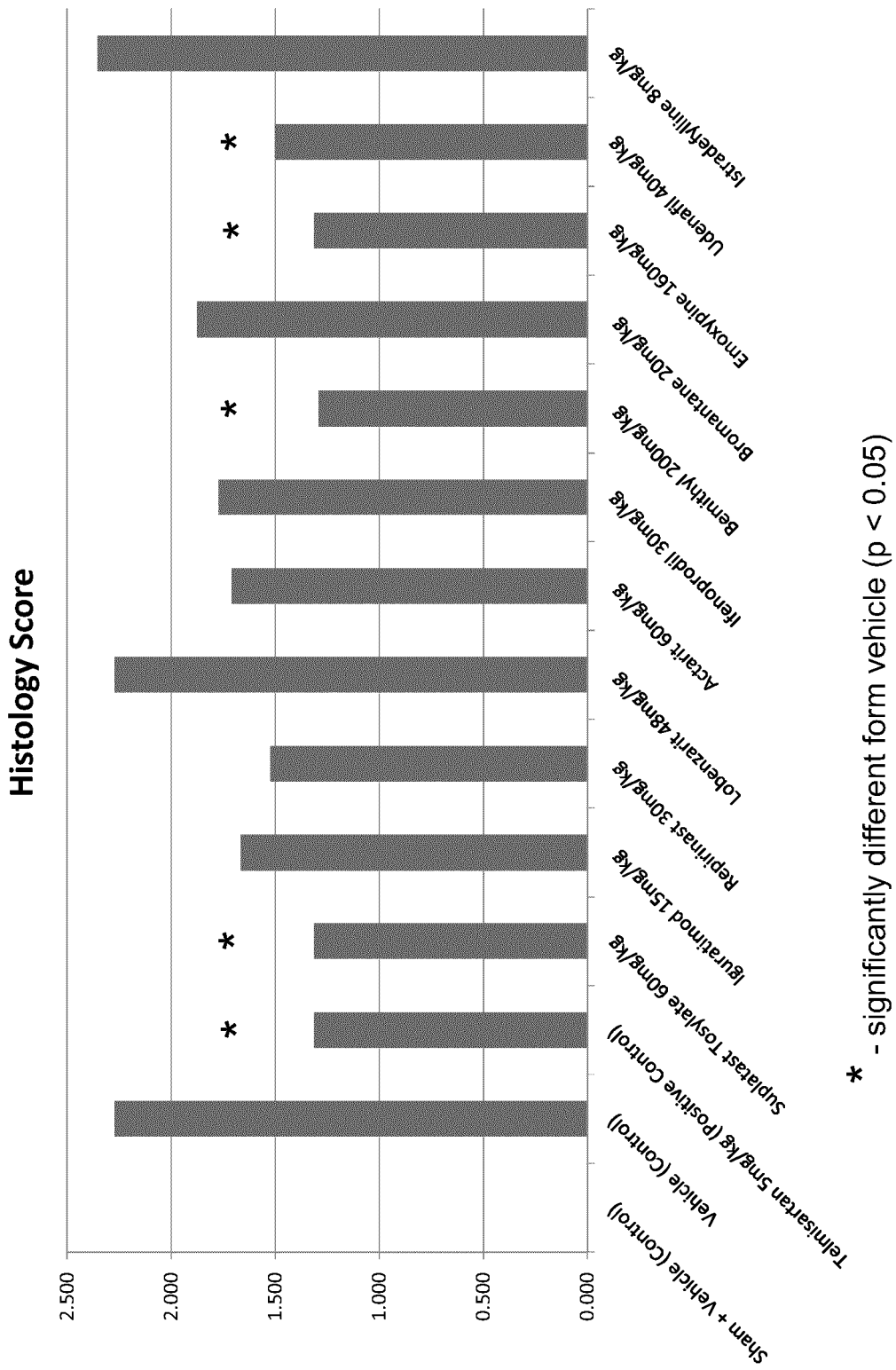
FIG. 5 shows an evaluation of renal fibrosis and interstitial damage with the level of fibrosis indicated by Histology Scores of 0 (normal), 1 (light), 2 (moderate) or 3 (severe) in three randomly selected fields of renal cross-sections stained with Sirius Red at ×20 magnification for each of the 14 study groups of C57BL/6 mice consisting of the sham surgery control group, the surgery vehicle control group, and the 12 treatment groups including the positive control treatment group.
Figure 6:
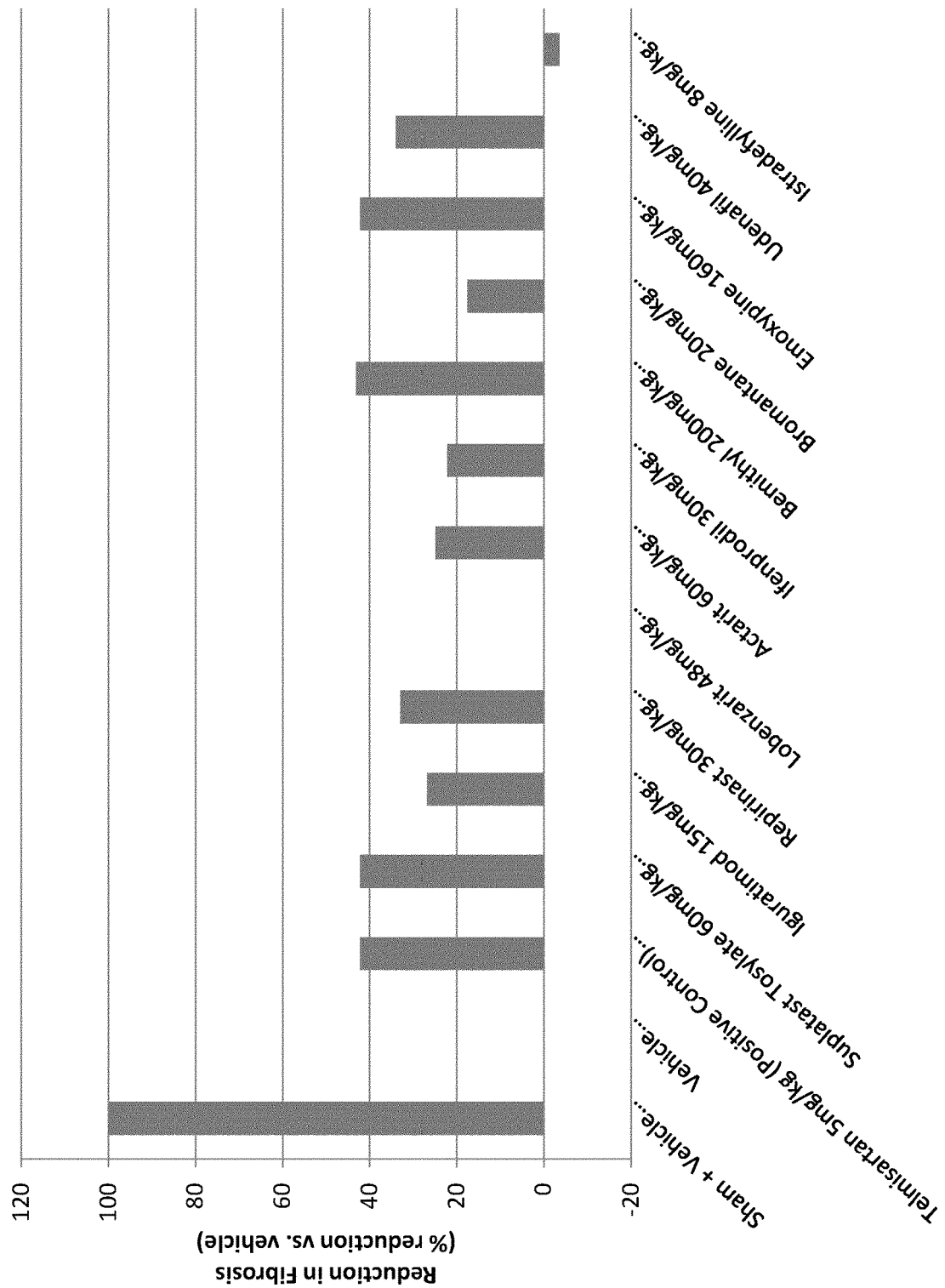
FIG. 6 shows the reduction in renal fibrosis for each the 14 study groups of C57BL/6 mice consisting of the sham surgery control group, the surgery vehicle control group, and the 12 treatment groups including the positive control treatment group.

Renal Fibrosis Evaluation: Renal fibrosis and interstitial damage was evaluated by histochemical staining of renal cross-sections with Sirius Red as previously described. The Histology Score of each study group consisted of the histology score average of all mice in each study group. Results are shown in Table 5 and FIGS. 5 and 6.

TABLE 5

Sirius Red Stain Scoring.

| | Histology Score | % Reduction Fibrosis (vs vehicle) |
|---|---|---|
| Sham + Vehicle | 0.00 | 100% |
| Vehicle | 2.27 | 0% |
| Telmisartan 5 mg/kg (Positive Control) | 1.31 | 42% |
| Iguratimod 15 mg/kg | 1.67 | 27% |
| Repirinast 30 mg/kg | 1.52 | 33% |
| Lobenzarit 48 mg/kg | 2.27 | 0% |
| Actarit 60 mg/kg | 1.71 | 25% |
| Suplatast Tosylate 60 mg/kg | 1.31 | 42% |
| Ifenoprodil 30 mg/kg | 1.77 | 22% |
| Bemithyl 200 mg/kg | 1.29 | 43% |
| Bromantane 20 mg/kg | 1.88 | 17% |
| Emoxypine 160 mg/kg | 1.31 | 42% |
| Udenafil 40 mg/kg | 1.50 | 34% |
| Istradefylline 8 mg/kg | 2.35 | −4% |

The p-values of all treatment groups were statistically significant except for the Lobenzarit and Istradefylline treatment groups.

The Histology Scores for treatment groups Suplatast Tosylate and Emoxypine were the same as the positive control treatment group.

The Histology Scores for the Bemithyl treatment group was decreased in comparison to the positive control treatment group Telmisartan.

In particular, Bemithyl (200 mg/kg), Emoxypine (160 mg/kg), Suplatast Tosylate (60 mg/kg), and Udenafil (40 mg/kg) showed significant reductions in kidney fibrosis. The positive control Telmisartan (5 mg/kg) also showed a significant reduction.

Conclusions

Oral administration of Bemithyl (200 mg/kg) showed significant improvement in kidney fibrosis and reduction in BUN compared to vehicle, and appeared to reverse the negative effects of UUO on body weight gain. Repirinast at 30 mg/kg and Bromantane at 20 mg/kg showed significant reductions in BUN compared to vehicle, while Udenafil (40 mg/kg), Emoxypine (160 mg/kg) and Suplatast Tosylate (60 mg/kg) showed significant reduction in fibrosis compared to vehicle.

Oral administration of Telmisartan at 5 mg/kg also showed reduction in BUN levels and fibrosis, though the former was not statistically significant. Telmisartan appeared to reduce the disparity in kidney size in the UUO-model, but the significance of this effect was not determined.

Example 2

Materials and Methods

In this example, healthy young female C57BL/6 mice were used for the study. At the commencement of the study, mice were between 9-12 weeks of age, weighing 23-25 g. All the mice were obtained from Charles River Laboratories.

The mice were maintained in a controlled environment with a temp 70-72° F., humidity 30-70%, with a photo cycle of 12 hours of light and 12 hours of dark. They were provided with Harlan Teklad 2018 standard maintenance mouse chow diet and drinking water ad libitium.

After five days of acclimatization, the mice were grouped according to their body weight. There were ten groups of ten mice each. Nine groups of ten mice each underwent UUO as described above and the other group of ten mice underwent a sham procedure to serve as a no-surgery control.

Following surgery, the mice were divided into 10 individual study groups of 10 mice each and, following post-surgical recovery, administered a once-daily oral treatment for 14 days. The mice in 8 of the 10 study groups had all received the UUO surgical ligation and were treated individually with a distinct pharmacologic compound as set out in Table 6. The mice in 2 of the 10 study groups were treated individually with a pharmaceutically acceptable vehicle with no active ingredient. The pharmaceutically acceptable vehicle in all groups was 0.5% carboxymethyl cellulose (CMC). All mice were sacrificed with $CO_2$ on post-surgical day 15.

TABLE 6

| Group | Description | N | ROA | Dose mg/kg | Dosign Volume | Dosing Frequency |
|---|---|---|---|---|---|---|
| 1 | Sham + vehicle (0.5% CMC) | 10 | PO | xxxx | 10 ml/kg | QD Days 1-14 |
| 2 | Surgery + Vehicle | 10 | PO | xxxx | 10 ml/kg | QD Days 1-14 |
| 3 | Surgery + Telmisartan | 10 | PO | 3 | 10 ml/kg | QD Days 1-14 |
| 4 | Surgery + Bemithyl | 10 | PO | 200 | 10 ml/kg | QD Days 1-14 |
| 5 | Surgery + Repirinast | 10 | PO | 90 | 10 ml/kg | QD Days 1-14 |
| 6 | Surgery + Repirinast | 10 | PO | 30 | 10 ml/kg | QD Days 1-14 |
| 7 | Surgery + Telmisartan + Bemithyl | 10 | PO | 3 + 200 | 10 ml/kg | QD Days 1-14 |
| 8 | Surgery + Telmisartan + Repirinast | 10 | PO | 3 + 30 | 10 ml/kg | QD Days 1-14 |
| 9 | Surgery + Cenicriviroc | 10 | PO | 40 | 10 ml/kg | QD Days 1-14 |
| 10 | Surgery + Bromantane | 10 | PO | 40 | 10 ml/kg | QD Days 1-14 |

The dose selected for the animal studies was determined by taking the maximum known human daily dose, dividing by the average weight of an adult (~60-70 kg) to get a human mg/kg dose. That number was multiplied by 12 to convert to a mouse dose based on conventional dosing tables. See Nair and Jacob, *J Basic Clin Pharm* March 2016-May 2016, 7(2):27-31.

The following measurements and assessments were taken for each mouse.

Body weight: The body weights were measured on days 1, 4, 7, 10 and 14 using a laboratory balance.

Serum collection: A blood sample was then collected from all mice and plasma analyzed for urea nitrogen and creatinine. Plasma was stored at −80° C. for possible future analysis.

Kidney weight: The UUO was then examined in situ to ensure that the surgical ligation ties remained patent. Both the ligated (UUO) and non-ligated kidneys were removed for analysis. Weights of both kidneys were measured using a laboratory balance.

Histopathology: Formalin-fixed kidney cross-section samples were subjected histopathological scoring with Sirius Red staining, and imaged at a magnification of ×20, using standard techniques. All three sections were stained and evaluated. The analysis was performed by a board-certified veterinarian pathologist. The presence of interstitial damage and severity score was assessed according to the following criteria: 0=normal; 1=light; 2=moderate; 3=severe.

The data are presented as the mean obtained from Microsoft Excel or GraphPad Prism version 5.00 for Windows (GraphPad Software, San Diego California USA). Data were analyzed using two-way ANOVA using Bonferroni and Tamhane post-tests. Differences between groups were considered significant at $p<0.05$.

Results

Figure 7:
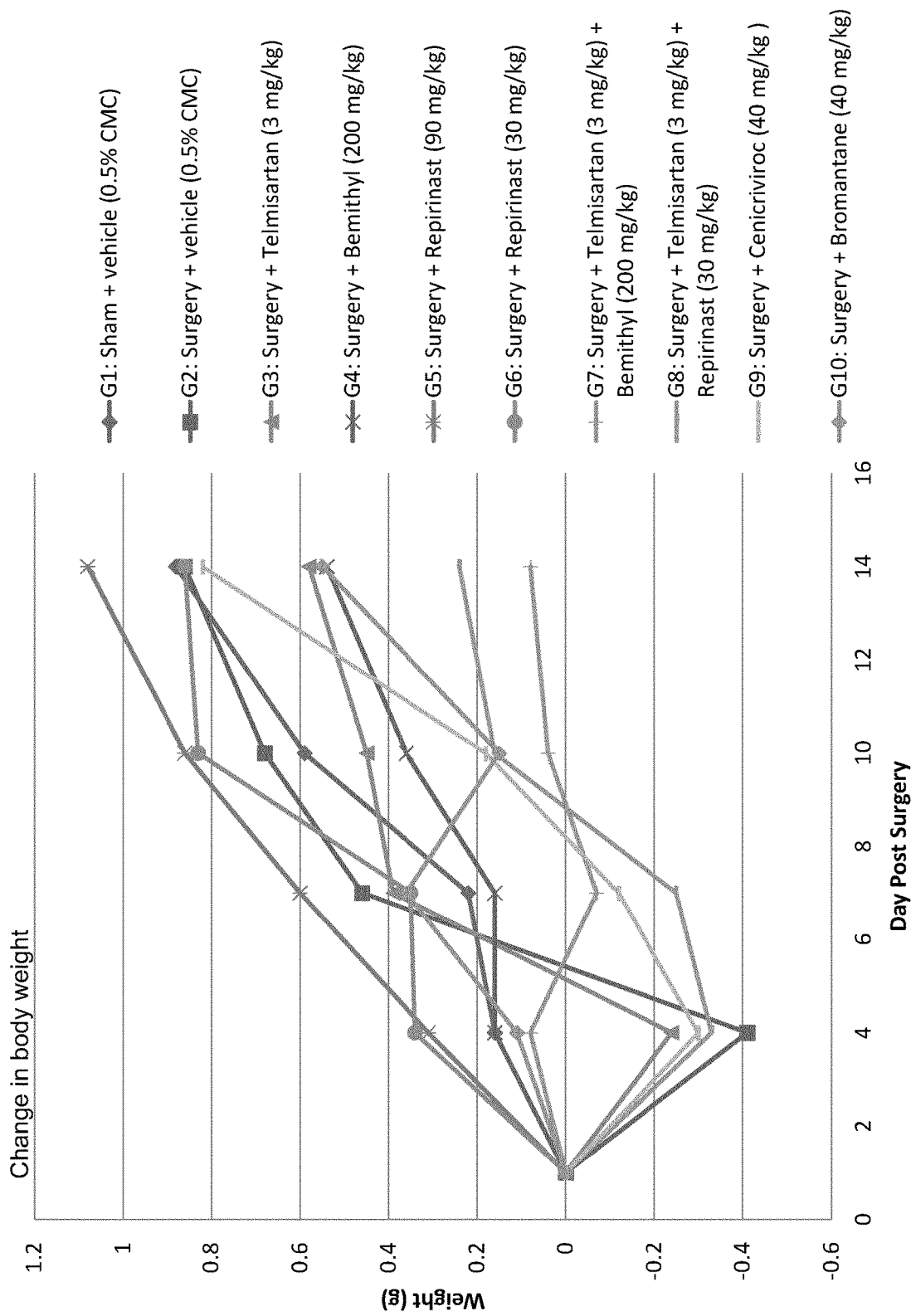
FIG. 7 shows a comparison of the change in mean body weight in grams for each of the 10 study groups of C57BL/6 mice from a second example consisting of the sham surgery control group "Sham+Vehicle (Control)", the surgery vehicle control group "Vehicle (Control)", and the 8 treatment groups including the positive control treatment group, Telmisartan.

Body Weight Evaluation: Results of the evaluation of mean body weight change are shown in FIG. 7 and Table 7. Body weights were measured on post-surgical days 1, 4, 7, 10 and 14 as previously described. The mean body weight change of each study group was calculated using the body weight average of all mice in each study group.

TABLE 7

Mean Body Weight Change Following Surgery (g)

| | | Change in body weight | | | | |
|---|---|---|---|---|---|---|
| Group | Treatment | Day 1 | Day 4 | Day 7 | Day 10 | Day 14 |
| 1 | Sham + Vehicle | 0 | 0.16 | 0.22 | 0.59 | 0.88 |
| 2 | Vehicle | 0 | −0.41 | 0.46 | 0.68 | 0.86 |
| 3 | Telmisartan (3 mg/kg) | 0 | −0.24 | 0.39 | 0.45 | 0.58 |
| 4 | Bemithyl (200 mg/kg) | 0 | 0.16 | 0.16 | 0.36 | 0.54 |
| 5 | Repirinast (90 mg/kg) | 0 | 0.31 | 0.60 | 0.86 | 1.08 |
| 6 | Repirinast (30 mg/kg) | 0 | 0.34 | 0.35 | 0.83 | 0.86 |
| 7 | Telmisartan (3 mg/kg) + Bemithyl (200 mg/kg) | 0 | 0.08 | −0.07 | 0.04 | 0.08 |
| 8 | Telmisartan (3 mg/kg) + Repirinast (30 mg/kg) | 0 | −0.33 | −0.25 | 0.16 | 0.24 |
| 9 | Cenicriviroc (40 mg/kg ) | 0 | −0.30 | −0.12 | 0.18 | 0.82 |
| 10 | Bromantane (40 mg/kg) | 0 | 0.11 | 0.36 | 0.15 | 0.55 |

A decrease in body weight gains was observed for the first 4 days in the vehicle group, after which these gains began to recover. In the groups treated with Repirinast (30 and 90 mg/kg), Bemithyl (200 mg/kg), Bromantane (40 mg/kg) and Telmisartan+Bemithyl (3 mg/kg+200 mg/kg), there was no initial decrease in body weight, and weight gain continued for the duration of the experiment. The mean body weight change on post-surgical day 14 for the Bemithyl treatment group was even greater than that of the sham surgery control group.

Figure 8:
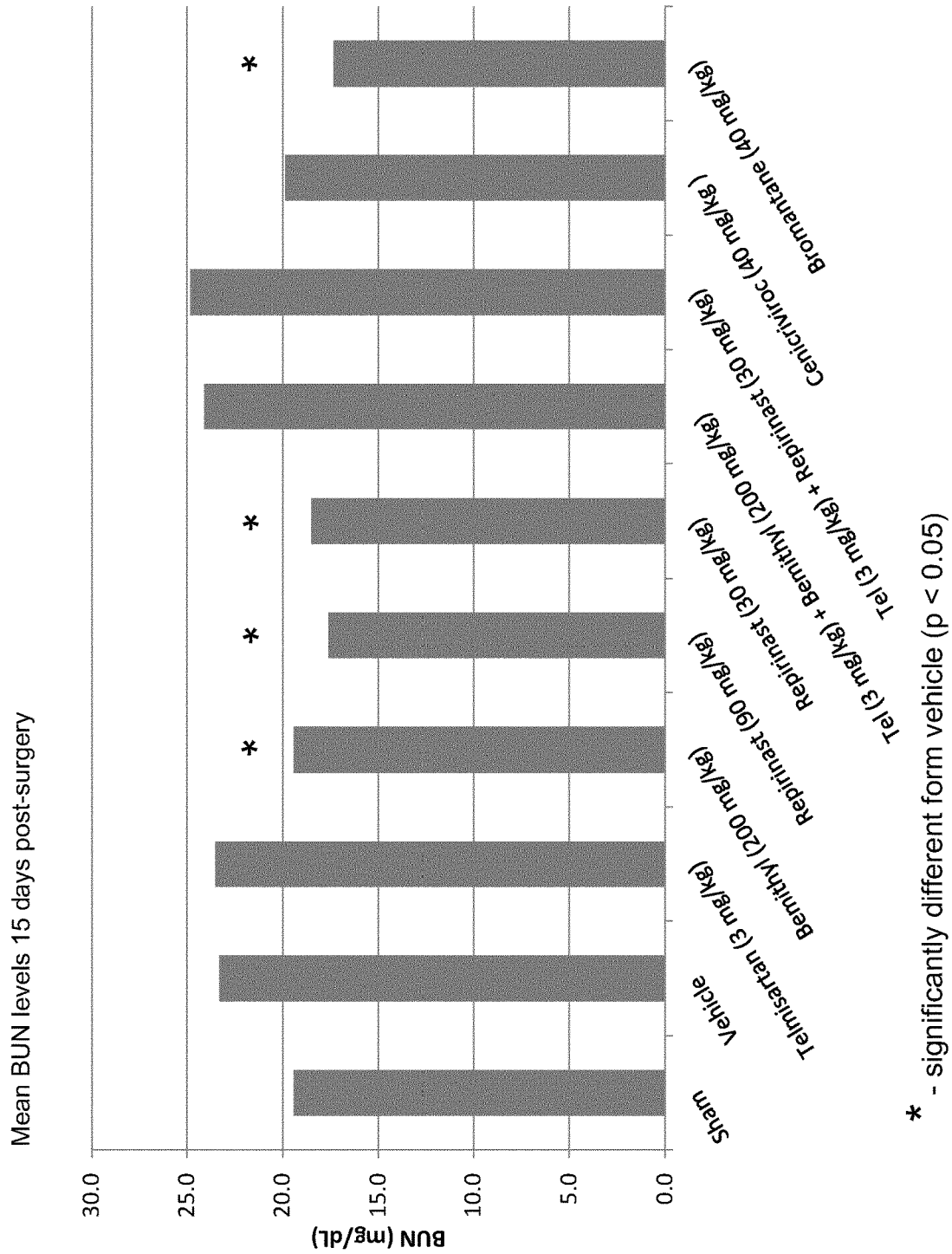
FIG. 8 shows an evaluation of renal function consisting of the plasma urea nitrogen (BUN) in mg/dL for each of the 10 study groups of C57BL/6 mice consisting of the sham surgery control group "Sham+Vehicle (Control)", the surgery vehicle control group "Vehicle (Control)", and the 8 treatment groups including the positive control treatment group.
Figure 9:
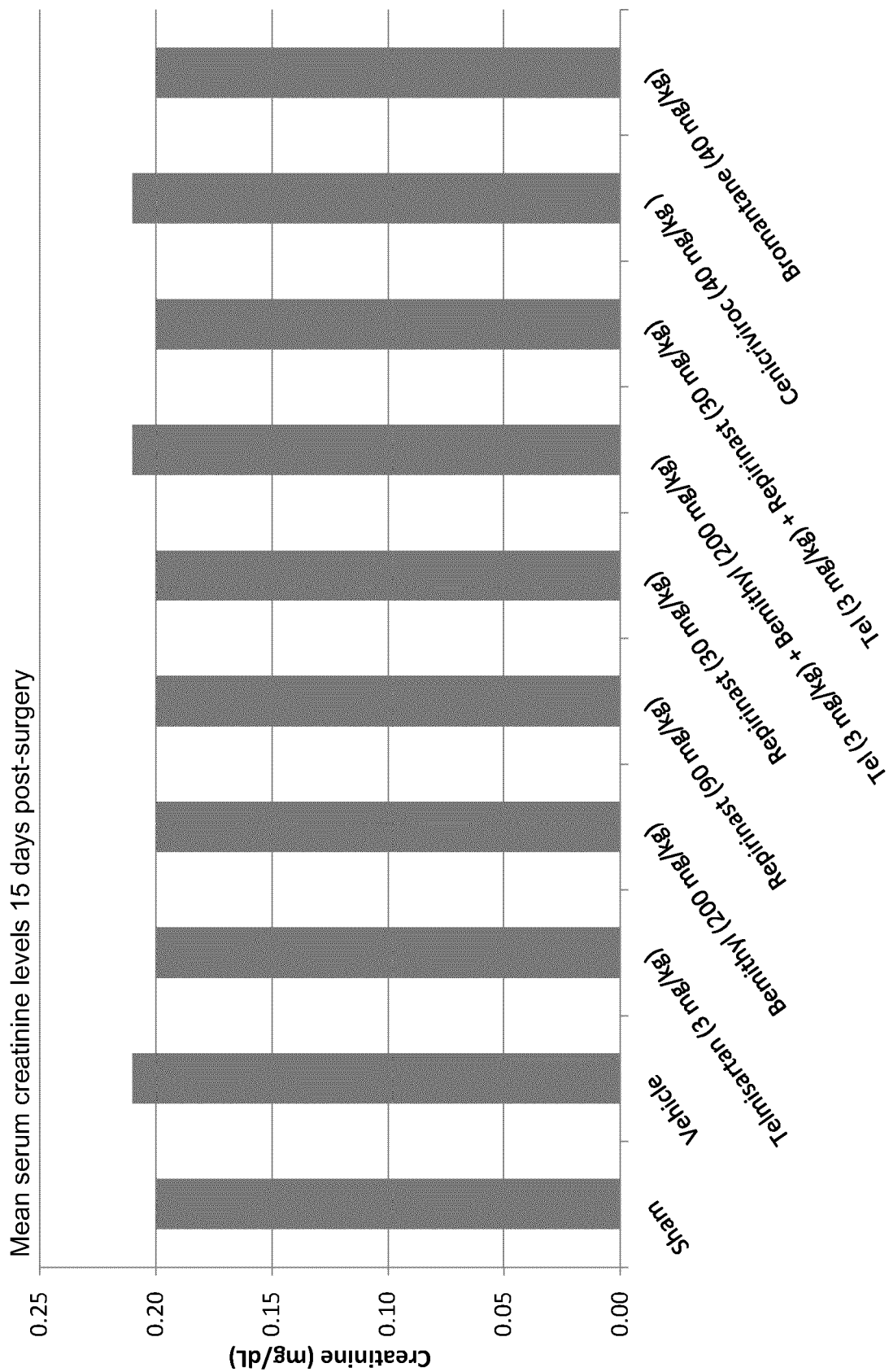
FIG. 9 shows an evaluation of renal function consisting of the Creatinine in mg/dL for each of the 10 study groups of C57BL/6 mice consisting of the sham surgery control group "Sham+Vehicle (Control)", the surgery vehicle control group "Vehicle (Control)", and the 8 treatment groups including the positive control treatment group.

Renal Function Evaluation: Renal function and disease progression was evaluated by BUN (blood urea nitrogen) as previously described. The BUN of each study group consisted of the BUN average of all mice in each study group. Results are shown in FIGS. 8 and 9 and Table 8.

TABLE 8

Results of Renal Function Evaluation.

| Group | Treatment | BUN | Creatinine |
|---|---|---|---|
| 1 | Sham + Vehicle | 19.4 | 0.20 |
| 2 | Vehicle | 23.3 | 0.21 |
| 3 | Telmisartan (3 mg/kg) | 23.5 | 0.20 |
| 4 | Bemithyl (200 mg/kg) | 19.4* | 0.20 |
| 5 | Repirinast (90 mg/kg) | 17.6*# | 0.20 |
| 6 | Repirinast (30 mg/kg) | 18.5*# | 0.20 |
| 7 | Telmisartan (3 mg/kg) + Bemithyl (200 mg/kg) | 24.1 | 0.21 |
| 8 | Telmisartan (3 mg/kg) + Repirinast (30 mg/kg) | 24.8 | 0.20 |
| 9 | Cenicriviroc (40 mg/kg) | 19.9 | 0.21 |
| 10 | Bromantane (40 mg/kg) | 17.3** | 0.20 |

For Tables 8:
*significantly different from vehicle following a Bonferroni post-hoc test;
following a Tamhane post-hoc test (p <0.05)

The urea nitrogen (BUN) and creatinine data are presented in FIGS. 2 & 3 and Table 3, respectively. Administration of Bemithyl (200 mg/kg), Repirinast (90 mg/kg and 30 mg/kg) and Bromantane (40 mg/kg) led to significant reductions in the level of BUN compared to vehicle. Cenicriviroc also reduced the level of BUN, but this reduction was not significant. Bromantane was the most effective compound tested, followed by Repirinast and Bemithyl. The positive control Telmisartan did not reduce levels of BUN, and when combined with Repirinast or Bemithyl appeared to mitigate the ability of these agents to reduce BUN levels. Bromantane was found to be superior to Telmisartan; otherwise the differences observed between the agents were not significant. There were no differences in the levels of serum creatinine in any of the groups tested.

Figure 10:
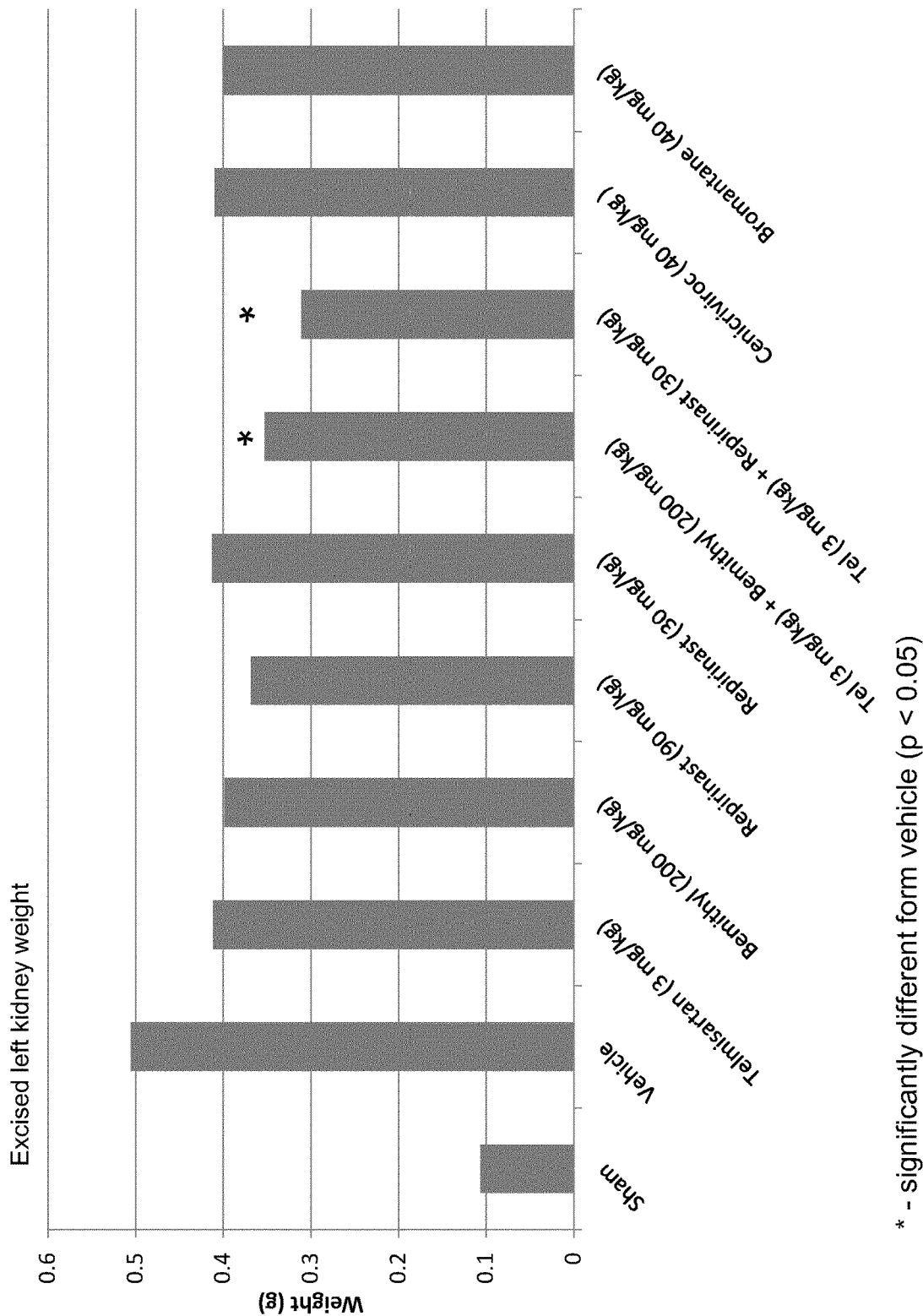
FIG. 10 shows the weight of the right kidney in grams for each of the 10 study groups of C57BL/6 mice consisting of the sham surgery control group "Sham+Vehicle (Control)", the surgery vehicle control group "Vehicle (Control)", and the 8 treatment groups including the positive control treatment group, Telmisartan.
Figure 11:
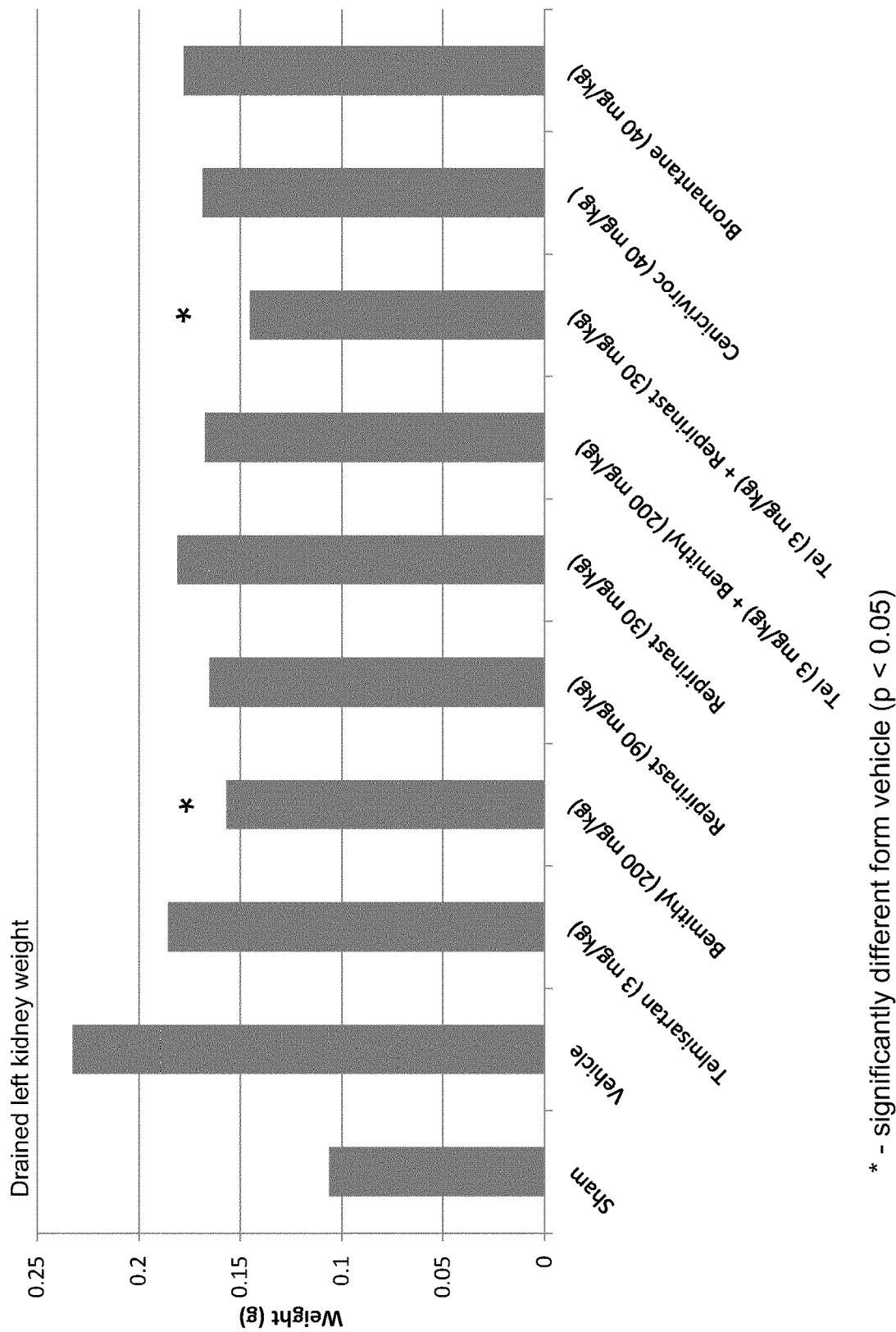
FIG. 11 shows the weight of the left kidney in grams for each of the 10 study groups of C57BL/6 mice consisting of the sham surgery control group "Sham+Vehicle (Control)", the surgery vehicle control group "Vehicle (Control)", and the 8 treatment groups including the positive control treatment group, Telmisartan.

Kidney Weight Evaluation: Kidney weight, which indicates functional and pathological changes in the kidney, was evaluated by measuring the weight of both the ligated (UUO) and non-ligated kidneys as previously described. The ligated and non-ligated kidney weights of each study group consisted of the respective kidney weight averages of all mice in each study group. Results are shown in Table 9 and FIGS. 10 and 11.

TABLE 9

Kidney Weights for Study Groups.

| Gp | Treatment | Excised Left Kidney (g) | Drained Left Kidney (g) | Right Kidney (g) |
|---|---|---|---|---|
| 1 | Sham + Vehicle | 0.106 | 0.106 | 0.1116 |
| 2 | Vehicle | 0.5054 | 0.2325 | 0.1888 |
| 3 | Telmisartan (3 mg/kg) | 0.411 | 0.1853* | 0.1263* |
| 4 | Bemithyl (200 mg/kg) | 0.398 | 0.1565 | 0.1333* |
| 5 | Repirinast (90 mg/kg) | 0.3681 | 0.1648 | 0.1378* |
| 6 | Repirinast (30 mg/kg) | 0.412 | 0.1808 | 0.1468* |
| 7 | Tel (3 mg/kg) + Bemithyl (200 mg/kg) | 0.3524* | 0.167 | 0.1242*# |
| 8 | Tel (3 mg/kg) + Repirinast (30 mg/kg) | 0.3102 | 0.145* | 0.1222* |
| 9 | Cenicriviroc (40 mg/kg) | 0.4091 | 0.1683 | 0.1342* |
| 10 | Bromantane (40 mg/kg) | 0.3995 | 0.1775 | 0.143* |

For Table 9:
*significantly different from vehicle following a Bonferroni post-hoc test;
following a Tamhane post-hoc test (p <0.05)

The weight of the left (ligated) kidney in the vehicle group was greatly increased. All of the tested compounds effected numerical reductions in the weight of the left kidney. The greatest reductions were achieved by the administration of Telmisartan (3 mg/kg) combined with Bemithyl (200 mg/kg) or Repirinast (30 mg/kg)—only these reductions were significant following the application of Bonferroni (for both) or Tamhane (for Repirinast) corrections. The combination of Telmisartan and Repirinast was also able to significantly reduce the weight of the drained left kidney compared to the vehicle group; a similar effect was observed for Bemithyl (200 mg/kg). During the experiment, the vehicle group also saw a significant increase in the weight of the right (unligated) kidney. All of the treatments tested were able to significantly reduce the weight of this organ.

Figure 12:
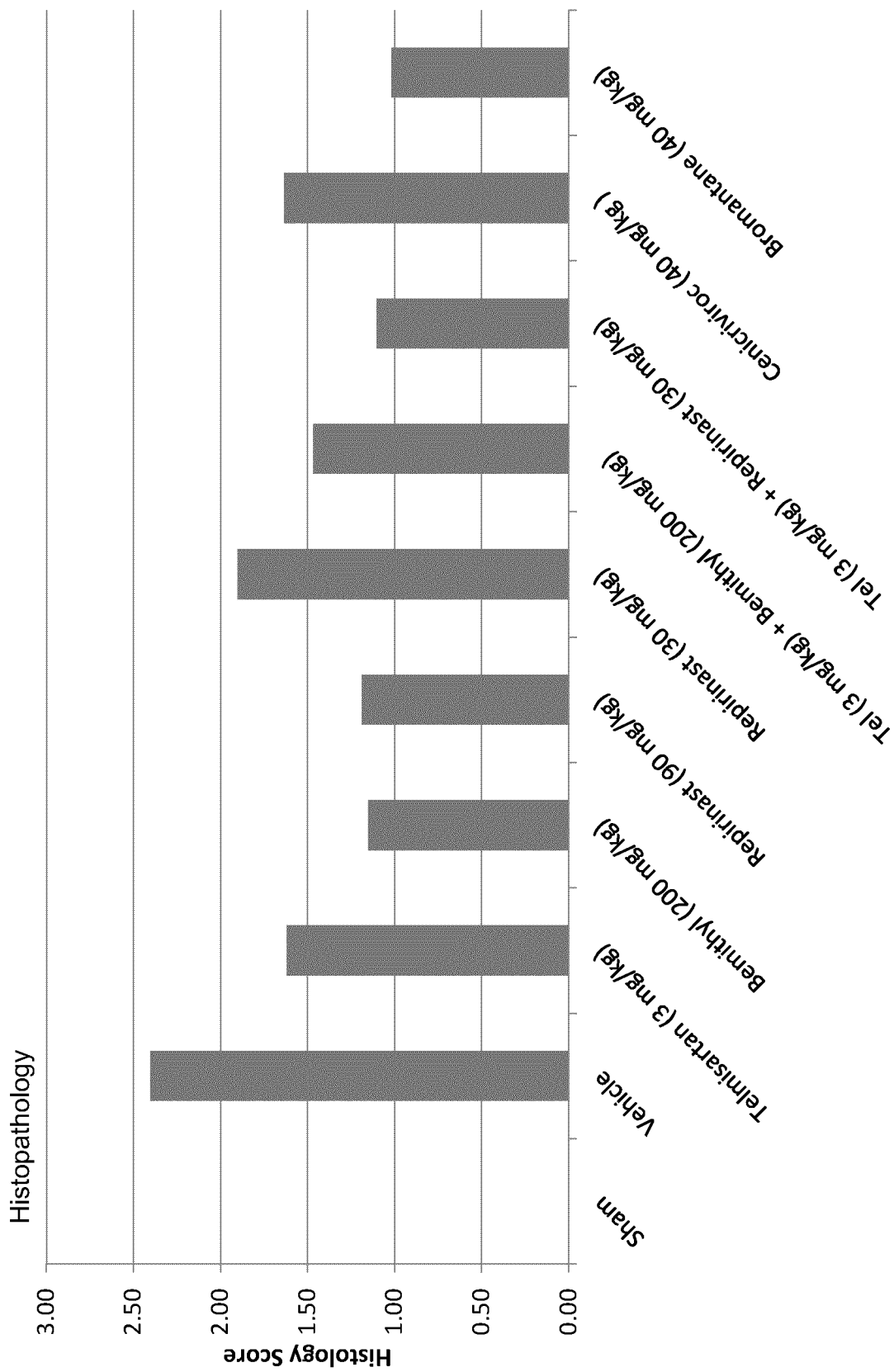
FIG. 12 shows an evaluation of renal fibrosis and interstitial damage with the level of fibrosis indicated by Histology Scores of 0 (normal), 1 (light), 2 (moderate) or 3 (severe) in three randomly selected fields of renal cross-sections stained with Sirius Red at ×20 magnification for each of the 10 study groups of C57BL/6 mice consisting of the sham surgery control group, the surgery vehicle control group, and the 8 treatment groups including the positive control treatment group.
Figure 13:
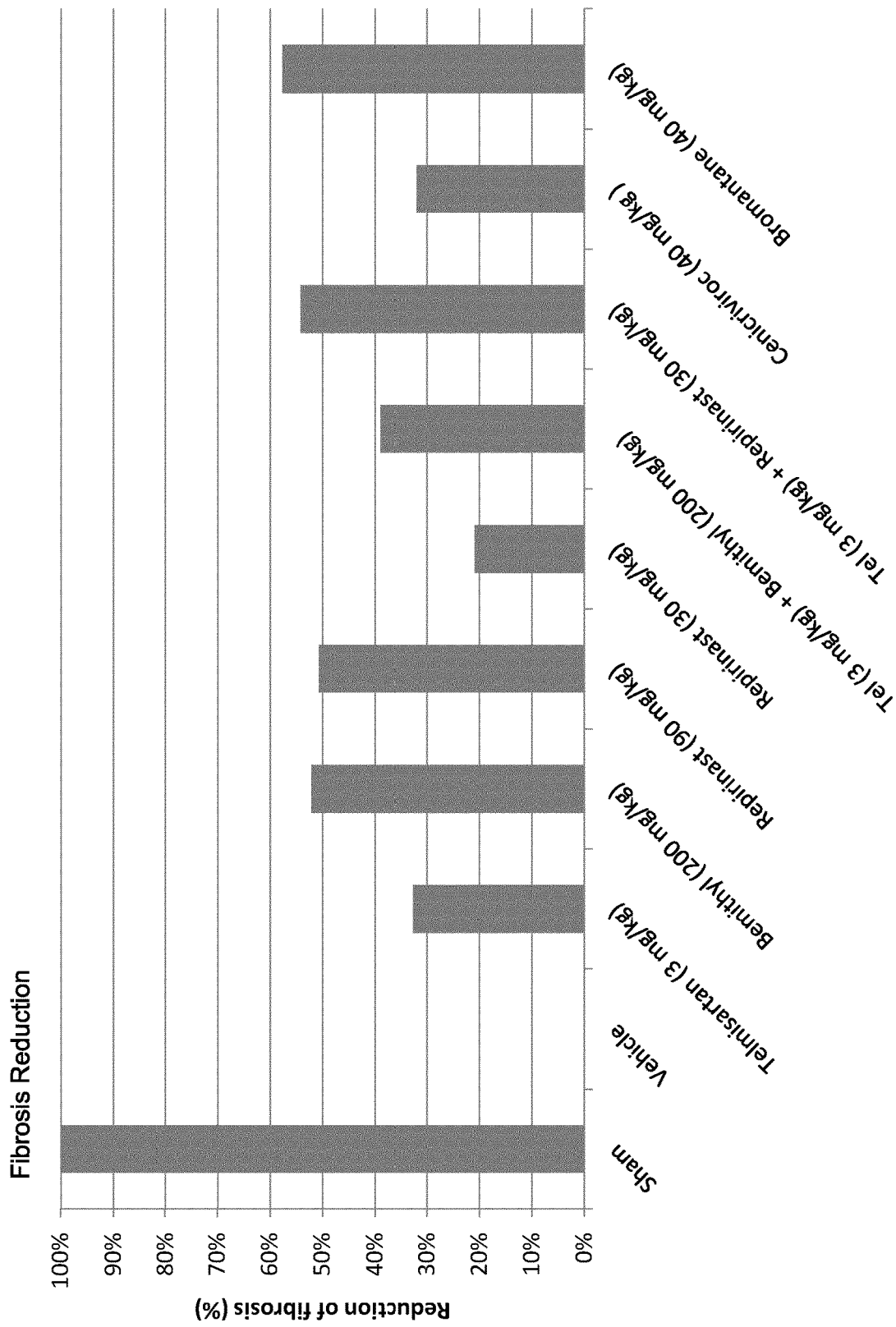
FIG. 13 shows the reduction in renal fibrosis for each the 10 study groups of C57BL/6 mice consisting of the sham surgery control group, the surgery vehicle control group, and the 8 treatment groups including the positive control treatment group.

Renal Fibrosis Evaluation: Renal fibrosis and interstitial damage was evaluated by histochemical staining of renal cross-sections with Sirius Red as previously described. The Histology Score of each study group consisted of the histology score average of all mice in each study group. Results are shown in Table 10 and FIGS. 12 and 13.

TABLE 10

Histology

| Group | Treatment | Histology Score | Reduction of fibrosis (%) (versus vehicle) |
|---|---|---|---|
| 1 | Sham + Vehicle | 0.00 | 100% |
| 2 | Vehicle | 2.40 | 0% |
| 3 | Telmisartan (3 mg/kg) | 1.62*# | 33% |
| 4 | Bemithyl (200 mg/kg) | 1.15** | 52% |
| 5 | Repirinast (90 mg/kg) | 1.19*# | 51% |
| 6 | Repirinast (30 mg/kg) | 1.90 | 21% |
| 7 | Telmisartan (3 mg/kg) + Bemithyl (200 mg/kg) | 1.47** | 39% |
| 8 | Telmisartan (3 mg/kg) + Repirinast (30 mg/kg) | 1.10** | 54% |
| 9 | Cenicriviroc (40 mg/kg) | 1.63*# | 32% |
| 10 | Bromantane (40 mg/kg) | 1.02*# | 58% |

Note:
The histology score for Bromantane was significantly lower than that for Telmisartan (after Bonferroni correction) and Cenicrivoc (after Bonferroni and Tamhane corrections) (p <0.05)

The agents Bemithyl (200 mg/kg), Repirinast (90 mg/kg) and Bromantane (40 mg/kg) as well as Telmisartan (3 mg/kg) in combination with either Bemithyl (200 mg/kg) or Repirinast (30 mg/kg) were able to significantly reduce the level of kidney fibrosis compared to vehicle, whereas lower dose Repirinast (30 mg/kg), Cenicriviroc (40 mg/kg) and the positive control Telmisartan (3 mg/kg) showed statistically insignificant improvements. Bromantane had the greatest numerical reduction in the histology score; by this measure Bromantane was superior to both Telmisartan (p<0.05 following Bonferroni post-correction) and Cenicrivoc (p<0.05 following either Bonferroni or Tamhane post-corrections.

Conclusions

Oral administration the test compounds Bemithyl (200 mg/kg), Repirinast (90 mg/kg) and Bromantane (40 mg/kg) showed significant improvement in kidney fibrosis and reduction in BUN compared to vehicle, and appeared to reverse the negative effects of UUO on body weight gain. Of these three agents, Bromantane offered the highest reductions in both fibrosis and BUN levels.

Oral administration of Telmisartan at 3 mg/kg did not show significant reductions in BUN levels or fibrosis. Telmisartan in combination with Repirinast (30 mg/kg) or Bemithyl (200 mg/kg) significantly reduced the size of the ligated kidney in the UUO-model.

Throughout the description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are consistent with the broadest interpretation of the specification as a whole.

What is claimed is:

1. A method for the treatment or prophylaxis of renal fibrosis or kidney disease in a subject, the method comprising administering:
   a therapeutically effective amount of Repirinast to the subject.
2. The method of claim 1, wherein the amount of Repirinast is between 0.5 to 20 mg per kg of the subject.
3. The method of claim 2, wherein the amount of Repirinast is between 1 to 10 mg per kg of the subject.
4. The method of claim 3, wherein the amount of Repirinast is about 2.5 mg per kg of the subject.
5. The method of claim 1, further comprising administering a therapeutically effective amount of Telmisartan to the subject.
6. The method of claim 5, wherein the amount of Telmisartan is between 0.1 to 5 mg per kg of the subject.
7. The method of claim 6, wherein the amount of Telmisartan between 0.1 to 1 mg per kg of the subject.
8. The method of claim 7, wherein the amount of Telmisartan is about 0.25 mg per kg of the subject.

* * * * *